(12) United States Patent
Forsell

(10) Patent No.: US 10,441,398 B2
(45) Date of Patent: Oct. 15, 2019

(54) IMPLANTABLE FLUID MOVEMENT DEVICE

(76) Inventor: Peter Forsell, Zug (CH)

( * ) Notice: Subject to any disclaimer, the term of this patent is extended or adjusted under 35 U.S.C. 154(b) by 738 days.

(21) Appl. No.: 12/864,702

(22) PCT Filed: Jan. 28, 2009

(86) PCT No.: PCT/SE2009/000039
§ 371 (c)(1),
(2), (4) Date: Jul. 27, 2010

(87) PCT Pub. No.: WO2009/096854
PCT Pub. Date: Aug. 6, 2009

(65) Prior Publication Data
US 2010/0312163 A1 Dec. 9, 2010

Related U.S. Application Data

(60) Provisional application No. 61/006,711, filed on Jan. 28, 2008.

(30) Foreign Application Priority Data

Oct. 10, 2008 (SE) ...................................... 0802154

(51) Int. Cl.
*A61M 5/00* (2006.01)
*A61F 2/00* (2006.01)
*A61M 1/00* (2006.01)
*A61M 27/00* (2006.01)

(52) U.S. Cl.
CPC ......... *A61F 2/0036* (2013.01); *A61M 1/0023* (2013.01); *A61M 1/0072* (2014.02); *A61M 27/002* (2013.01); *A61F 2250/0001* (2013.01); *A61M 2210/1078* (2013.01)

(58) Field of Classification Search
USPC .... 604/7–10, 93.01, 95.01, 175, 264, 891.1, 604/892.1; 607/51, 132; 623/23.66
See application file for complete search history.

(56) References Cited

U.S. PATENT DOCUMENTS

| 3,575,158 | A | * | 4/1971 | Summers | ............... A61F 2/0036 128/DIG. 25 |
| 3,713,441 | A | * | 1/1973 | Thomas | .................... A61F 2/06 604/175 |
| 3,752,162 | A | * | 8/1973 | Newash | ........................ 604/175 |
| 3,783,454 | A | * | 1/1974 | Sausse | ..................... A61F 2/04 623/23.66 |
| 3,818,511 | A | * | 6/1974 | Goldberg et al. | ............ 623/1.31 |

(Continued)

FOREIGN PATENT DOCUMENTS

| WO | WO 98/50099 | 11/1998 |
| WO | 2008055248 A2 | 5/2008 |

OTHER PUBLICATIONS

International Search Report for PCT/SE2009/000039, dated Apr. 27, 2009.

(Continued)

*Primary Examiner* — Bradley H Philips

(57) ABSTRACT

An implantable fluid movement device is provided. The device is adapted to move body fluid from one part of the body of a patient to another part of the body and further adapted to secure the tube end of the fluid movement device to a location inside a treated patient.

22 Claims, 27 Drawing Sheets

(56) References Cited

U.S. PATENT DOCUMENTS

| | | | |
|---|---|---|---|
| 3,953,897 A * | 5/1976 | Chevallet | A61F 2/042 623/23.65 |
| 4,217,664 A * | 8/1980 | Faso | 606/108 |
| 4,240,434 A * | 12/1980 | Newkirk | A61F 2/2412 137/242 |
| 4,610,658 A | 9/1986 | Buchwald et al. | |
| 4,629,458 A * | 12/1986 | Pinchuk | A61F 2/06 623/1.33 |
| 5,057,075 A | 10/1991 | Moncrief et al. | |
| 5,480,434 A * | 1/1996 | Eckstein | A61B 17/11 128/898 |
| 5,645,860 A * | 7/1997 | Knapp, Jr. | A61K 35/38 424/551 |
| 5,741,234 A * | 4/1998 | Aboul-Hosn | A61B 17/3423 604/174 |
| 5,902,336 A | 5/1999 | Mishkin | |
| 5,984,956 A * | 11/1999 | Tweden | A61B 17/11 623/1.36 |
| 6,007,510 A * | 12/1999 | Nigam | A61F 9/00781 604/8 |
| 6,007,576 A * | 12/1999 | McClellan | A61F 2/064 623/23.64 |
| 6,171,610 B1 * | 1/2001 | Vacanti | A61F 2/28 424/426 |
| 6,485,435 B1 * | 11/2002 | Bakal | 600/562 |
| 6,689,085 B1 | 2/2004 | Rubenstein et al. | |
| 6,772,011 B2 | 8/2004 | Dolgin | |
| 7,011,624 B2 | 3/2006 | Forsell | |
| 7,311,690 B2 * | 12/2007 | Burnett | 604/9 |
| 7,699,830 B2 * | 4/2010 | Martin | A61M 1/0058 137/315.24 |
| 7,722,665 B2 * | 5/2010 | Anwar | A61B 17/11 623/1.36 |
| 8,158,002 B1 * | 4/2012 | Lupton et al. | 210/650 |
| 8,961,448 B2 * | 2/2015 | Forsell | B01D 46/0065 604/9 |
| 9,694,165 B2 * | 7/2017 | Forsell | B01D 46/0065 |
| 9,789,290 B2 * | 10/2017 | Forsell | B01D 46/0065 |
| 2003/0074049 A1 * | 4/2003 | Hoganson et al. | 623/1.13 |
| 2003/0163079 A1 * | 8/2003 | Burnett | A61M 27/002 604/9 |
| 2003/0208247 A1 * | 11/2003 | Spinelli et al. | 607/51 |
| 2004/0073155 A1 * | 4/2004 | Laufer | A61B 8/12 604/8 |
| 2005/0009178 A1 * | 1/2005 | Yost et al. | 435/399 |
| 2005/0142163 A1 * | 6/2005 | Hunter | A61B 17/11 424/423 |
| 2006/0127246 A1 | 6/2006 | Forsell | |
| 2007/0293807 A1 * | 12/2007 | Lynch | A61F 9/00781 604/8 |
| 2009/0036820 A1 * | 2/2009 | Dakin | A61B 17/11 604/9 |
| 2010/0312164 A1 | 12/2010 | Forsell | |
| 2010/0318116 A1 | 12/2010 | Forsell | |
| 2010/0318117 A1 | 12/2010 | Forsell | |
| 2010/0318118 A1 | 12/2010 | Forsell | |
| 2010/0324591 A1 | 12/2010 | Forsell | |
| 2017/0304597 A1 * | 10/2017 | Forsell | B01D 46/0065 |

OTHER PUBLICATIONS

U.S. Appl. No. 12/864,695 (Forsell), filed Jul. 27, 2010.
U.S. Appl. No. 12/864,706 (Forsell), filed Jul. 27, 2010.
U.S. Appl. No. 12/864,714 (Forsell), filed Jul. 27, 2010.
U.S. Appl. No. 12/864,724 (Forsell), filed Jul. 27, 2010.
U.S. Appl. No. 12/864,828 (Forsell), filed Jul. 27, 2010.

* cited by examiner

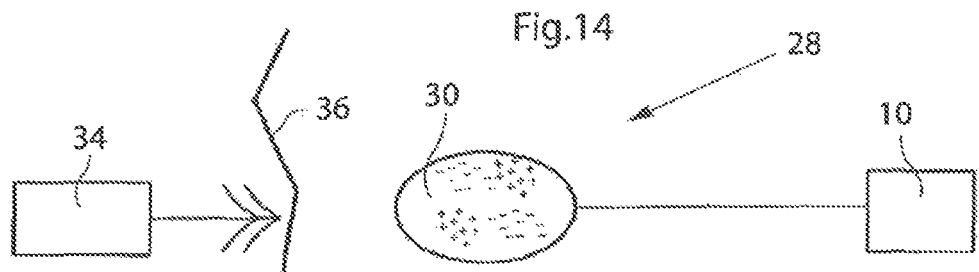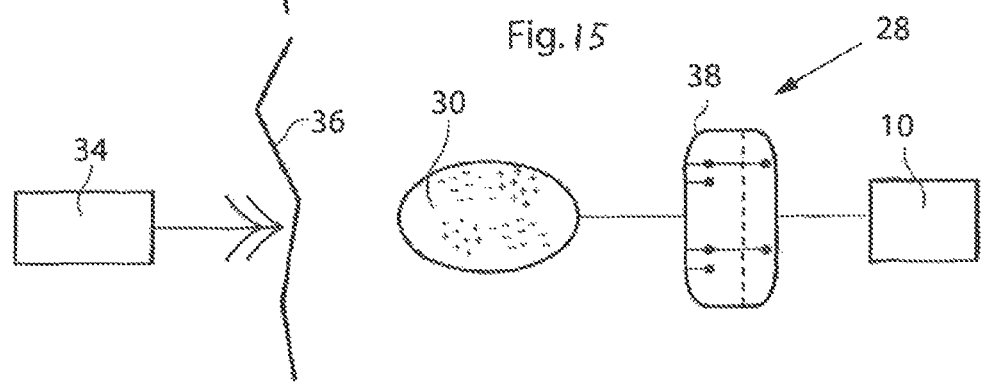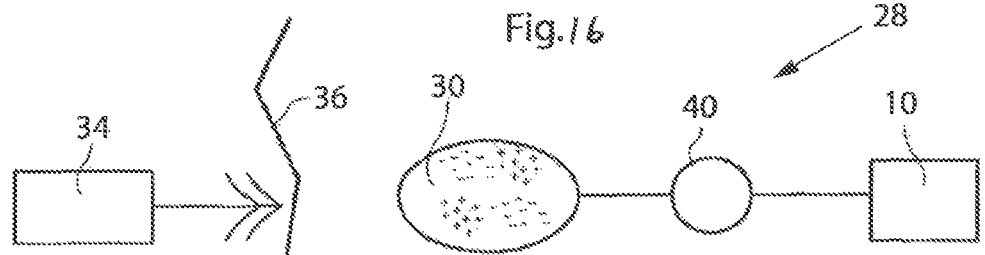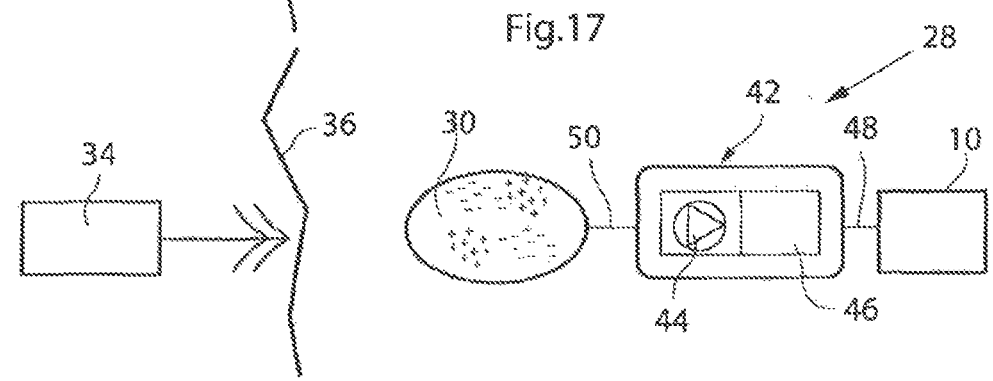

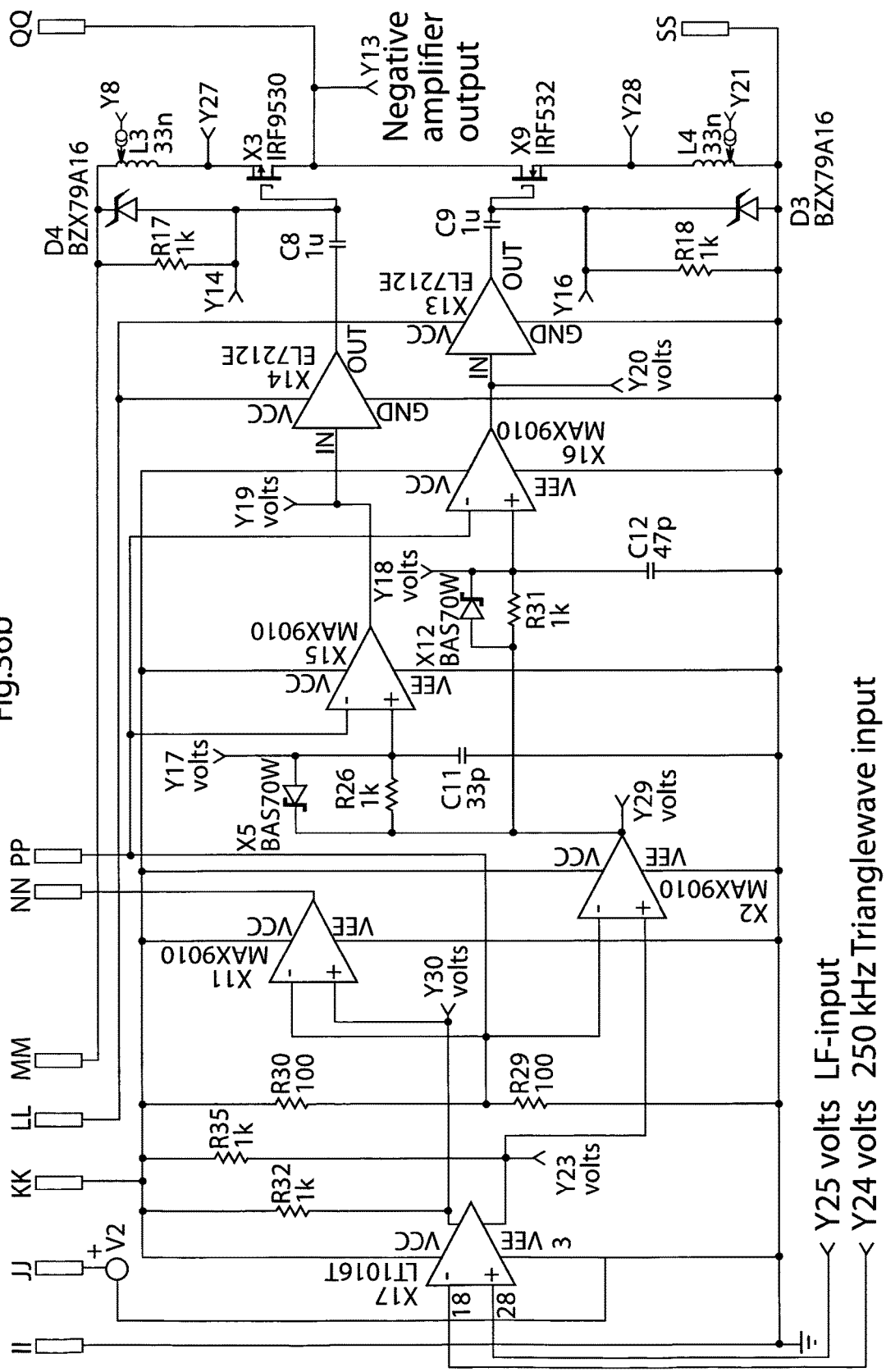
Fig.36b"

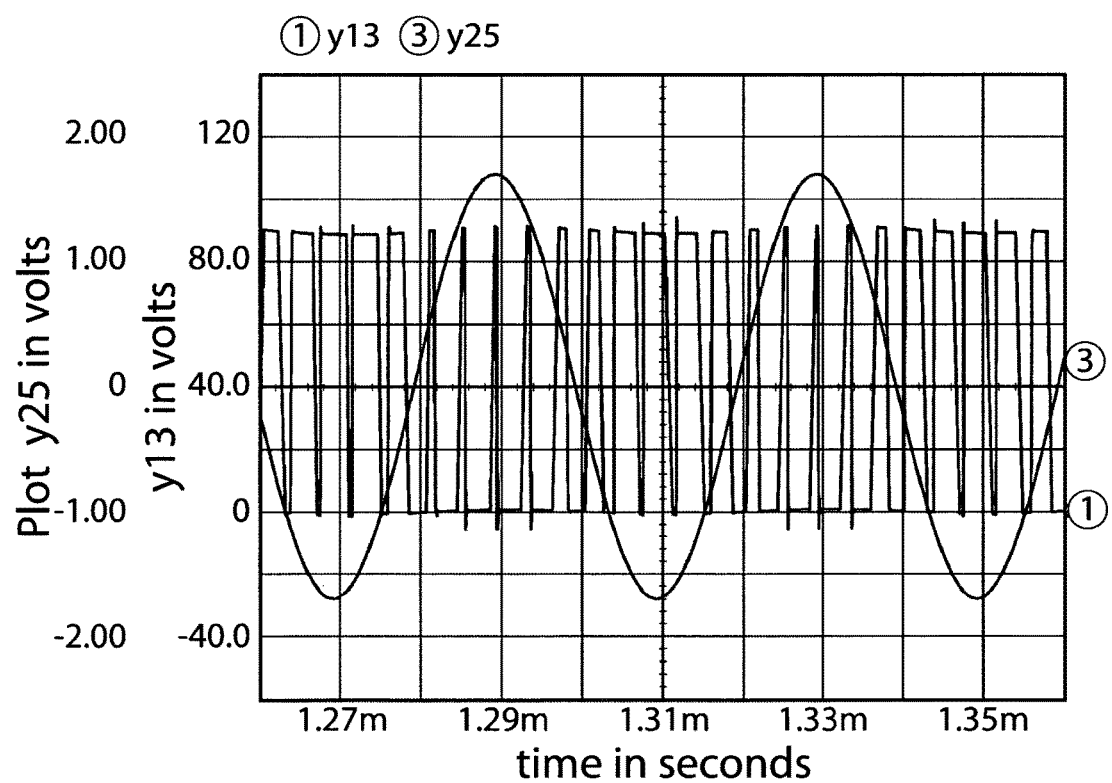

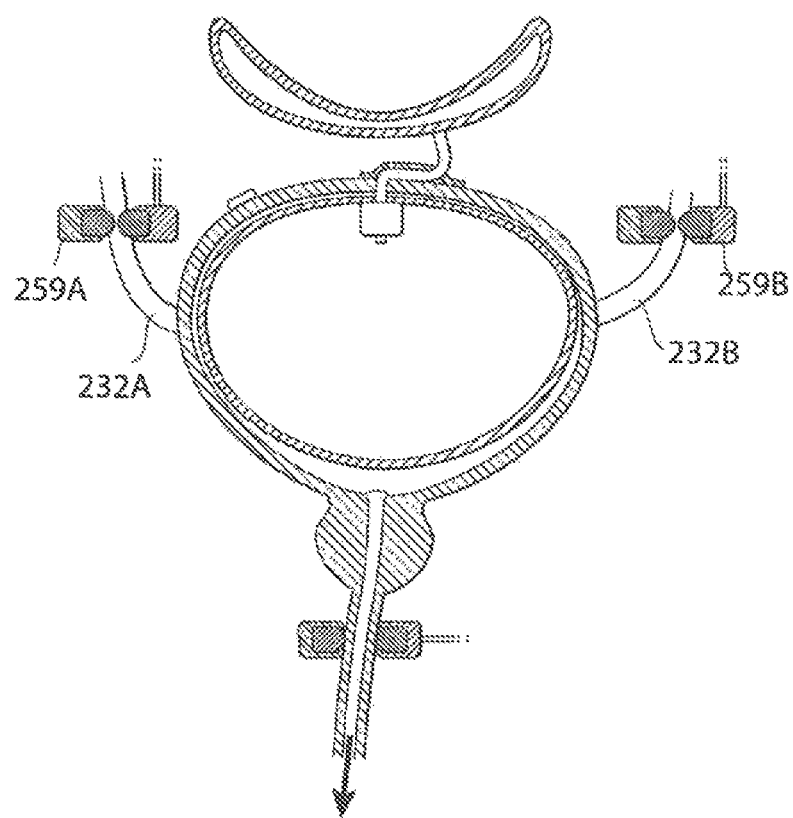

IMPLANTABLE FLUID MOVEMENT DEVICE

This application is the U.S. national phase of International Application No. PCT/SE2009/000039 filed 28 Jan. 2009 which designated the U.S. and claims priority to U.S. Provisional Application No. 61/006,711 filed 28 Jan. 2008 and Swedish Patent Application No. 0802154-5 filed 10 Oct. 2008, the entire contents of each of which are hereby incorporated by reference.

TECHNICAL FIELD

The present invention relates to a method and a device for moving a fluid within the body.

BACKGROUND

Body fluid drains are used at so-called drainage sites for draining fluids from cavities in a patient's body, typically during and after surgical procedures. The drainage site may be a natural body cavity or orifice or may be surgically formed.

The drain device used for draining fluid from the body typically comprises a tube extending from the treatment area within the body through the skin of the patient and ending in a manual pump located outside the body. The pump is associated with a reservoir for storing the drained fluid. The reservoir is then emptied at suitable time intervals by manually compressing the reservoir.

A drain can be required for shorter or longer periods of time depending on the condition for which the drain is used. In particular when the drain is used for a longer period of time the drains existing today are cumbersome to use and impractical for the patient who is required to move the drain with him/her when moving around.

Fluid can also be moved within the body in a hydraulic treatment system, wherein the fluid is hydraulic treatment fluid instead of a body fluid, delivered from the treatment area, which in this case may be a reservoir adapted to hold hydraulic treatment fluid.

Also, U.S. Pat. No. 7,195,608 describes a drainage device for moving fluid to the urine bladder.

The drainage device described in U.S. Pat. No. 7,195,608 describes an element for securing an end of the drainage device to the urine bladder. However, securing element suffers from a number of potential drawbacks. In particular there is a risk that the securing element does not provide a tight and lasting sealing whereby there is a risk that drained fluid ends up outside the urine bladder, which of course is undesired.

Hence, there exists a need for a drain that is less cumbersome to use and which enables a patient to more easily move around while still being attached to the drain. There is also a need for an efficient securing element that enables a tight and secure sealing for a drainage device.

SUMMARY

It is an object of the present invention to overcome or at least reduce some of the problems associated existing fluid movement devices, such as drainage devices or hydraulic treatment devices.

It is another object of the present invention to provide a fluid movement device that enables a patient to more easily move around while still being attached to the drain.

It is yet another object to provide a fluid movement device that can be efficiently secured.

At least one of the above objects is obtained by the method, apparatus, device and system as set out in the appended claims. Thus, by providing an implantable drain adapted to move body fluid or a hydraulic reservoir with hydraulic treatment fluid to move hydraulic fluid, from one part of the body to another part of the body, a fluid movement device that which is completely implanted and which does not have any mechanical structure penetrating through the skin of the patient is obtained.

The apparatus for drainage of a body fluid or movement of hydraulic treatment fluid in a human or mammal patient in accordance with the present invention comprises a fluid movement device for pumping hydraulic treatment fluid or body fluid. The fluid movement device is powered by an energy source and may be powered by any suitable means such as an electrical or a hydraulic motor. At least one connecting tube is connected to the fluid movement device so that the fluid movement device and the tube form a drainage or hydraulic arrangement. The arrangement is adapted to be implanted inside the body of the patient, and placed so that the tube interconnects one part of the body with another part of the body and where fluid movement device is adapted to suck body fluid from the one part of the body via the tube to the other part of the body. Hereby an implantable fluid movement device is obtained which can pump body or hydraulic fluid from a treatment area to another part of the body where the fluid can be absorbed or transported out from the body in a normal way.

The implantable fluid movement device in accordance with the present invention can be used to move body fluid between different parts of the body depending on the type of body fluid being drained. For example and without limitation the fluid movement device can be adapted to drain urine from the urine accumulating renal part of the kidney, and moving the urine via at least one tube to the urine bladder. The fluid movement device can also be adapted to drain liquid from the hydrocephalus in the brain area, and moving it to the abdomen. The fluid movement device can also be adapted to drain liquid from ascites in the abdomen, and moving it to the lymphatic system of the body or to the urine bladder. Also, the fluid movement device can also be adapted to drain liquid from the thoraxial cavity, and moving the liquid to the abdomen.

Depending on the type of treatment and where the body fluid is sucked from and to where in the body the fluid is delivered the tubes used may be shaped to suit the particular treatment.

In accordance with one embodiment a method of securing a connecting tube for use in an implantable device is provided. The tube is adapted to move body fluid from one part of the body, via the at least one connecting tube to another part of the body, the connecting tube having a distal end adapted to be located in the bladder of the human or mammal patient for drainage of a body fluid or hydraulic treatment fluid from a treatment area of the human or mammal patient into the bladder, the method comprising the steps of:
  opening a hole in the bladder,
  placing the end of the tube in the bladder.
  securing the tube on the outside of the bladder by invaginating the tube using sutures or staples, thus creating a tunnel around the tube, wherein said tube comprising a net material secured to said tube, in the part of the tube end at a distance from said tube end, the further method comprising, placing the net material in connection to the opening of the invaginated tunnel, and securing the net material to the outside of the bladder.

The bladder can be the urine bladder or the peritoneum. The same method can also be used for securely fastening a tube into other organs.

In accordance with one embodiment a tube adapted to be inserted in a luminal or bladder organ of a patient, said tube adapted to enter said organ in a tube passageway. The tube comprises a combined securing and sealing device adapted for long term closing of the tube passageway and for long term securing the tube onto an organ. The combined securing and sealing device can comprise a patch comprising a net mounted onto the tube. The net can be adapted to a seal of overgrowth of human fibrotic tissue over the whole net and the patched part of said organ, thereby completely sealing said net and attaching said net to said organ, thus sealing around said tubular passageway. In accordance with one embodiment a net structure is provide with openings less than 2.5 mm, preferable 0.5 mm, to allow said tissue overgrowth.

A specific embodiment of a hydraulic treatment system is presented below.

In one embodiment an apparatus for treating urinary retention of a patient by discharging urine from the urinary bladder, comprising an expandable member adapted to be implanted inside the urinary bladder of the patient, and an implantable control device for controlling the volume of the expandable member, the control device being adapted to be connected to the expandable member through the wall of the urinary bladder is provided. As a result of the expansion of the expandable member urine is discharged from urinary bladder through the urethra.

The expandable member is preferably releasably attached to the control device with quick coupling, such as snap-lock fitting or the similar and further member is designed with a capacity to assume a shape which admits its transportation through urethra. The expandable member can comprise a bellow or a similar structure undergoing controlled expansion and collapse.

Further, the expandable member is hydraulically controlled and comprises a cavity for hydraulic fluid and the control device comprises a reservoir for hydraulic fluid. The expandable member and the control device are accordingly adapted to be hydraulically connected through the wall of urinary bladder. For this purpose, the control device preferably comprises a tube to establish hydraulic connection and for transporting the hydraulic fluid between the reservoir and the cavity.

The control device of the apparatus can comprises an operation device for transporting hydraulic fluid to and from the cavity and the reservoir. In one mode of operation, the expandable member is adapted to be emptied by the pressure exerted by urine of the urinary bladder to transport the hydraulic fluid from the cavity to the reservoir. The operation device is capable of transporting hydraulic fluid to cavity of the expandable member to obtain a suitable urinary pressure for discharging urine. Also a urinary pressure of at least 50 cm water pressure for discharging urine can be provided.

The operation device can be powered, In one embodiment the operation device is a powered pump. Further, the operation device can comprise or being connected to an injection port, to calibrate the amount of hydraulic fluid. The operation device can also be manually operated by an injection port which is operated from outside the body by filling or emptying said injection port.

In addition the apparatus can comprise implantable restriction devices adapted to close the ureters when discharging urine from the urinary bladder in order to prevent any urinary backflow towards the kidneys. Preferably, these restriction devices open and close by the activity of the operation device.

The apparatus can also comprise a restriction device adapted to open and close the urethra to assist patients having an impaired urinary sphincter function.

The control device can further comprise a control assembly adapted to be implanted subcutaneously or in the abdominal cavity in the patient for connection to other parts of the control device. The control assembly comprises a source of energy for powering the operation device and other energy consuming parts of the control device. These parts are further described in the context of the system according to invention comprising the recited apparatus. The control assembly can further comprise an injection port for receiving hydraulic fluid, connected to the reservoir.

The apparatus can also comprise an implantable pressure sensor for measuring the urinary pressure in the urinary bladder direct or indirect, such as measuring the pressure inside the implantable member.

The hydraulic fluid can comprise an agent for counteracting microbial growth, such as an antibiotic.

In order to further assist urinary discharge, the control device can further comprise an implantable device for electrically stimulating muscles of the urinary bladder to contract the same, to co-operate with the expandable member to discharge urine from the urine bladder.

Also, the electrically stimulating device can comprise a plurality of electrode strips attached to muscles of the urinary bladder. In an alternative, the apparatus can comprise a second hydraulic connection between the expandable member and the reservoir. The second connection is dimensioned so that the pumps pumping volume capacity is clearly much larger than the emptying capacity of said second connection, when open. According to this alternative arrangement, the expandable member is adapted to be emptied by the pressure exerted by urine of the urinary bladder to transport the hydraulic fluid from the cavity to the reservoir by said second connection.

The present invention also relates to a method implanting the described apparatus, which comprises inserting a needle-like tube into the abdomen of the patient; filling the abdomen with gas through said tube, thereby expanding the abdominal cavity; placing at least two laparoscopic trocars in the patient's body and inserting a camera through one of said trocars into the abdomen; inserting at least one dissecting tool through a trocar and dissecting an area of at least one portion of the urinary bladder of patient; incising an opening in the urinary bladder wall; placing an expandable member inside the urinary bladder; placing a control device outside the urinary bladder; and interconnecting the expandable member and the control device with an interconnection device. The method also comprises tunnelling by suturing the urinary bladder wall to itself in order to immobilize the interconnecting device in position penetrating the urinary bladder wall while establishing a hydraulic connection between a cavity of the expandable member and a reservoir of the control device. Further, the method comprises placing net adapted to support in-growth of tissue with so it at least partially covers the tunnelling.

The present invention further extends to a method of operating the apparatus according to any that comprises activating a control assembly of the control device; increasing the volume of the expandable member; and discharging urine through the urethra. The method can further comprises the step activating the restriction devices to temporarily close the ureters and/or a step comprising activating the restriction device to temporarily release its restriction of the urethra or the neck of the urine bladder. In the method a control assembly can receive a signal from a pressure sensor measuring the urinary pressure in the urinary bladder or expandable member, said control assembly comprising an alarm system adapted to present an alarm signal for the patient, being able to activate said control assembly with a signal from a control unit controlled from external to the patient, such as a wireless remote control or an subcutaneously implantable switch. The method can further comprise the step of activating a pump for transporting hydraulic fluid from said reservoir to the expandable member.

The present invention sin yet another embodiment extends to a method of replacing an expandable member in the previous described apparatus for treating urinary retention comprising the steps of inserting an instrument adapted to operate on the expandable member through the urethra; releasing the expandable member from the control device; displacing the collapsed expandable member with the instrument; and transporting the collapsed expandable member through the urethra and out of the body. Further, the method comprises inserting a new, collapsed expandable member through the urethra; displacing the expandable member to a coupling position with control device; and attaching the expandable member to the control device with a quick coupling.

The present invention also relates to a system treating urinary incontinence comprising the previously described apparatus. Parts or components of system are described in the following sections of the description and should be regarded as applicable with any apparatus described above. In a one embodiment, the system comprises at least one switch implantable in the patient for manually and non-invasively controlling the apparatus In another embodiment, the system comprises a wireless remote control for non-invasively controlling the apparatus.

In one embodiment, the system comprises a hydraulic operation device for operating the apparatus.

In one embodiment, the system comprises comprising a motor or a pump for operating the apparatus.

Further embodiments are defined by the dependent claims.

BRIEF DESCRIPTION OF THE DRAWINGS

The present invention will now be described in more detail by way of non-limiting examples and with reference to the accompanying drawings, in which:

FIG. 14 is a schematic diagram of a cleaning system.

FIGS. 15-30 show various embodiments based on the system of FIG. 14.

FIG. 36c-d are graphs showing different waveforms of signals in the amplifier of the ultrasonic embodiment.

FIG. 42-43 describes a hydraulic treatment embodiment for emptying the urine bladder.

DETAILED DESCRIPTION

Figure 1A:
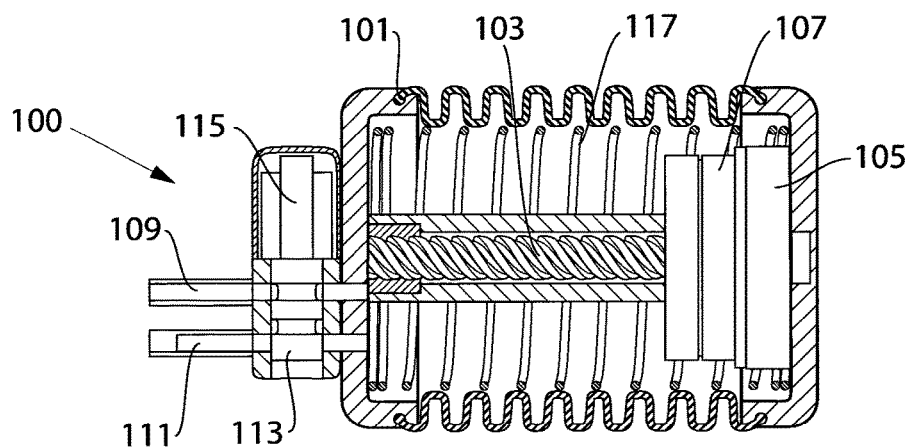
FIGS. 1a and 1b are views of an implantable fluid movement device in accordance with a first embodiment.
Figure 1B:
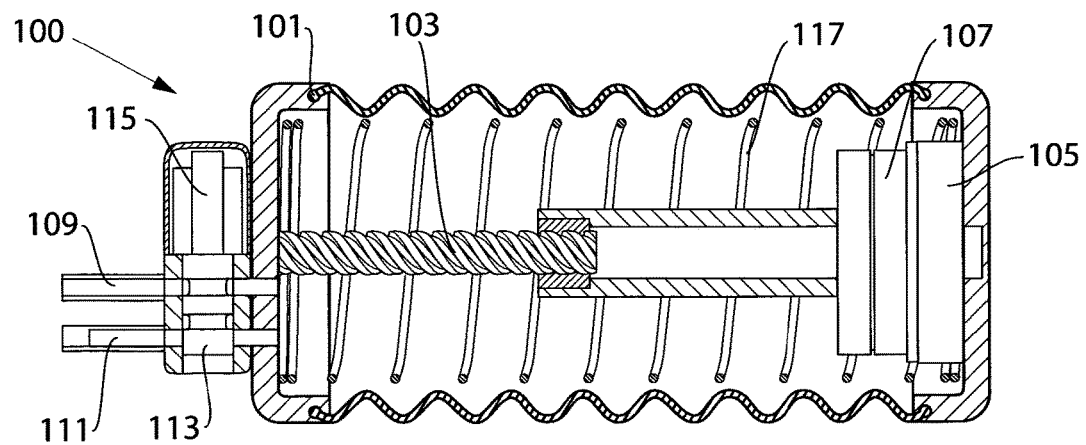

In FIGS. 1a and 1b a view illustrating an implantable fluid movement device 100. The device 100 comprises a bellow 101 adapted to move between a compressed position in which the bellow has a small inside volume and an expanded position in which the bellow has a larger inside volume. The view in FIG. 1a shows the bellow in a compressed position and the view in FIG. 1b shows the bellow in an expanded position.

The device 100 further comprises a member such as screw 103 adapted to compress the bellow 101. The screw 103 is accordance with one embodiment driven by a motor 105. The motor may many type of suitable motor including but not limited an electrical motor and a hydraulic motor. In accordance with one embodiment the motor is associated with a clutch 107 for regulating the power applied to the screw 103.

The inside of the bellow 101 is adapted receive and eject body fluid. The body fluid enters the bellow via an inlet 109 when the bellow expands. The fluid exits the bellow 101 via an outlet 111 when the bellow is compressed. In order for the fluid to only enter the bellow via the inlet when the bellow expands, a valve 113 is provided to prevent fluid to enter via the outlet 111 during the expansion phase. Similarly, the valve 113 is adapted to prevent fluid to exit via the inlet 109 when the bellow is compressed. The valve 113 is controlled by a control member 115 such as a solenoid.

The inlet and outlet are shaped to have tubes (not shown) fitted thereon. The tube connected to the inlet is preferably shaped and adapted to be placed in a treatment area from which body fluid is to be removed. The tube connected to the outlet is preferably shaped and adapted to be placed in a delivery area to which body fluid is to be moved from the treatment area.

During operation the device is adapted to compress the bellow in a compression phase during which fluid is ejected from the device 100 via the outlet tube to the delivery area for example by driving the motor to drive the screw. In a preferred embodiment a spring 117 is also compressed during the compression phase. During operation the device is further adapted to expand the bellow in an expansion phase during which fluid is sucked into the device 100 via the inlet tube from the treatment area for example by driving the screw in the opposite direction. In a preferred embodiment the spring 117 drives the bellow to expand during the expansion phase. When treating a patient the compression phase and expansion phase are continuously repeated whereby body fluid is removed from the treatment area to the delivery area.

Figure 2:
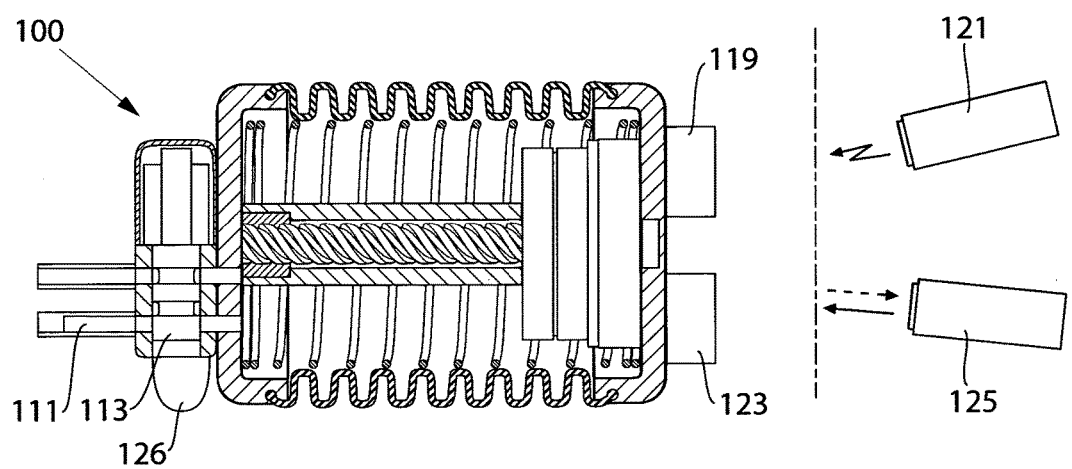
FIG. 2 is a view of an implantable fluid movement device in accordance with a second embodiment.

In FIG. 2 the device 100 is shown as supplemented with a control unit 119 for controlling the operation of the device 100. The control unit 119 can receive and transmit signals for a remote unit 121. The unit 121 is typically located outside the body when the device 100 is implanted inside a patient. In addition the device can be provided with a chargeable power source 123 connected to the motor. The power source 123 is adapted to receive wireless power from a second power source 125 which typically is located outside the patient when the implantable device 100 is implanted in a patient. Hereby the power source 123 can be recharged at suitable time intervals thereby removing the need for replacing the power source.

In order to prevent or remove a possible occlusion in the tube the fluid movement device can be provided with a backward release member 126 adapted to generate a backward pressure of fluid or air in the tube for removing or preventing a possible occlusion in the tube. The backward pressure is preferably repeatedly according to a predetermined time schedule. In accordance with one embodiment the release member comprises a pre-pressurized reservoir of air and a valve adapted to release a puff of air in the tube. In accordance with another embodiment the device 100 is adapted to move fluid or air in the tube in the reversed direction thereby creating a reverse flow for prevent or remove a possible occlusion in the tube. This can for example be obtained by controlling the valve 113 to a reversed more of operating so that fluid exits the device 100 via the inlet. In accordance with yet another embodiment a reservoir of the drainage is pre-pressurized by the pump, and a valve of the device is adapted to release a puff of fluid or air in the tube extending from the pre-pressurized reservoir when the pressure has reached a predetermined level.

Figure 3:
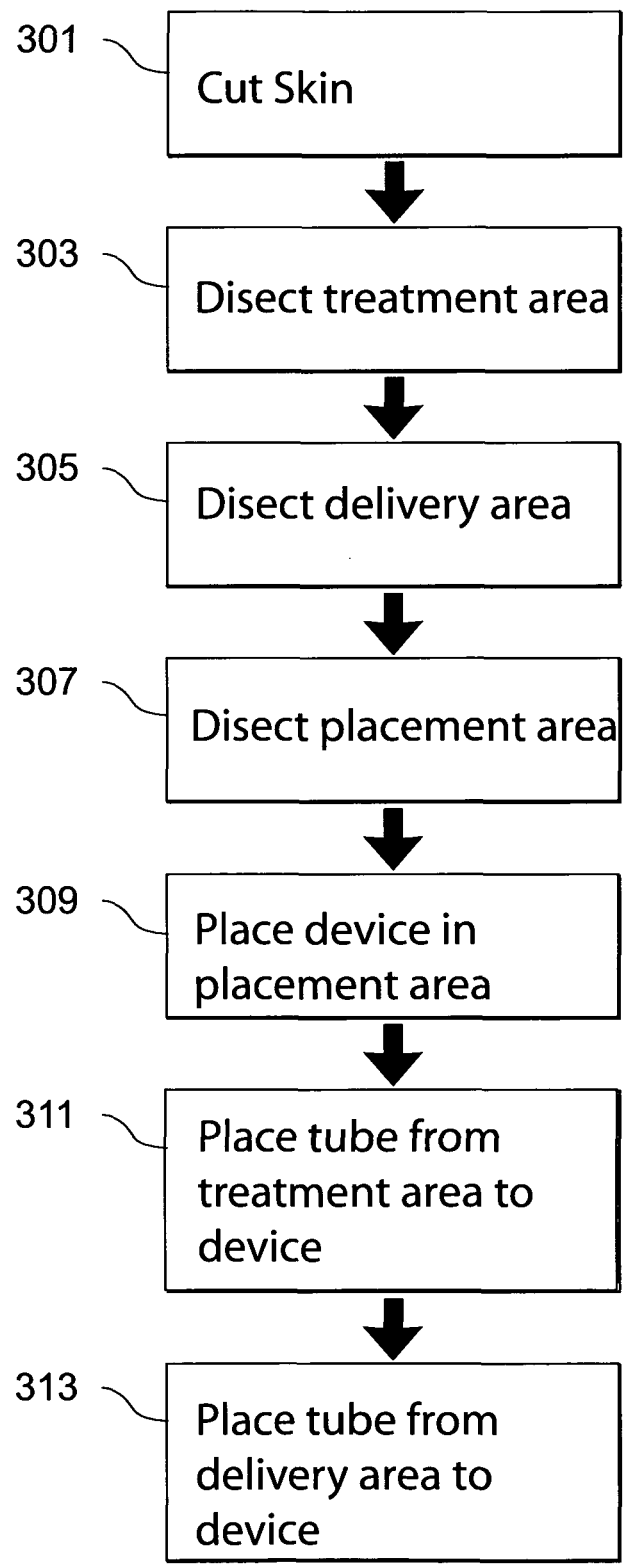
FIG. 3 is a flowchart illustrating different steps performed when implanting an implantable fluid movement device.

In FIG. 3 a flowchart illustrating step performed when implanting the device 100 in a patient. First in a step 301 skin is cut at locations corresponding to the location where the device is to be placed and where the tubes leading to and from the device are going to be placed. Next, in a step 303 the area from which body fluid is to be removed, the treatment area is dissected. Then, in a step 305, the area to which body fluid is to be moved, the delivery area, is dissected. Thereupon, in a step 307, the area where the device is to be placed, the placement area is dissected, if the placement area is different from the treatment area and the delivery area. Next, in a step 309 the device is placed in the placement area and the tubes extending between the device and the treatment area and the delivery area are put into place in steps 311 and 313, respectively.

In accordance with one embodiment a cleaning device 10 is inserted in the flow passageway from the treatment area to where the fluid is moved, I.e. the delivery area.

Figure 4:
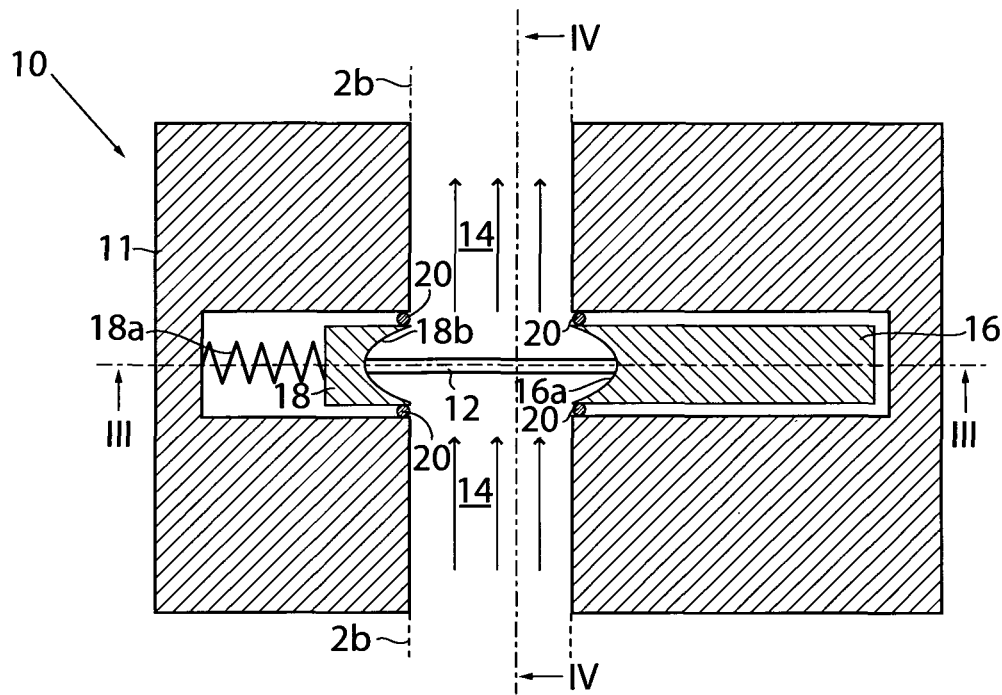
FIG. 4 is a sectional view of a cleaning device according to the invention.
Figure 5:
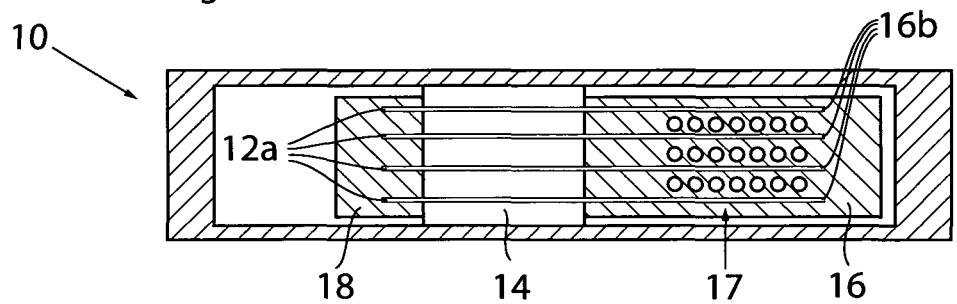
FIG. 5 is a cross sectional view of the cleaning device of FIG. 4 taken along the line III-III before a cleaning operation.
Figure 6:
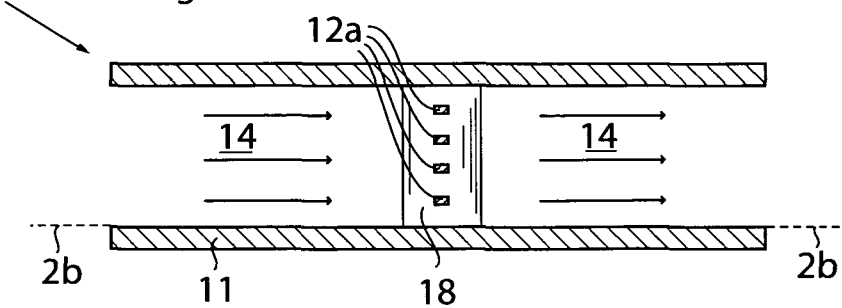
FIG. 6 is a sectional view of the cleaning device of FIG. 4 taken along the line IV-IV.

The design of a first preferred embodiment of a cleaning device 10 will now be described in detail, with reference to FIGS. 4-6. FIG. 4 shows a sectional view wherein the cleaning device 10 is provided in the flow passageway provided by a tube 2b. A filter 12 is provided across the flow passageway 14 formed in a housing 11 with the function of stopping particles brought forward in tube 2b by the flow, indicated by arrows in the figure. In this preferred embodiment, the filter 12 comprises a plurality of preferably equally spaced strips 12a of some suitable material, such as bio-compatible metal or plastic. These strips 12a are preferably arranged mutual parallel.

The distance between two adjacent strips is small enough to stop any particles larger than some predetermined size. In accordance with one embodiment the distance is less than 2 millimeters, and even less than 1.0 millimeters. Also for some applications the distance could be larger. The flow passageway 14 can have an essentially square cross-sectional shape or can it can take any suitable shape, such as rectangular or circular.

By providing a plurality of strips 12a as a filter across the flow passageway 14, a laminar flow is achieved downstream of the filter, which is can be advantageous. The flow configuration can be further enhanced by giving the plurality of strips 12a a desired cross-sectional shape, although the rectangular shape shown in FIG. 6 will be adequate for most purposes.

A first piston 16 is provided movable in a direction essentially perpendicular to the direction of the flow passageway 14, i.e., essentially perpendicular to the direction of the flow. This first piston 16 is driven by some suitable actuator means, such as pressurized air, a solenoid arrangement, an electrical servo motor or the like. A motor could be used to build up a stored power that could be released very fast, one example being a spring. In a preferred embodiment, pressurized air acts as the actuator means, since by latching the piston by means of a suitable latching means for the piston, building up the air pressure, and subsequently releasing the piston, very high speed of the piston is achieved, with enables short cleaning times of the filter.

The outer end portion of the first piston 16, i.e., the end portion facing the flow passageway 14, is essentially flush with the wall of the flow passageway in a non-active state of the cleaning device 10. Also, the outer end portion is provided with a concave portion or recess 16a (exaggerated in the figures) in order to act as a particle capturing means, as will be explained below.

The strike range of the first piston 16 is preferably such that it extends all way across the flow passageway 14, as will be explained below with reference to FIGS. 7-10. A number of channels 16b corresponding to the number of strips 12a is provided in the first piston 16 to accommodate the strips when the first piston is in an extended position.

The first piston 16 is also provided with a plurality of through holes 17 in the direction of the flow passageway. These through holes will allow a flow through the flow passageway also during a cleaning operation, as will be explained below with reference to FIG. 11.

A second piston 18 is provided across the flow passageway 14 from the first piston 16. Also this second piston 18 is movable in a direction essentially perpendicular to the direction of the flow passageway 14 and is biased in the direction thereof by means of a spring 18a, for example. Likewise, the outer end portion of the second piston is provided with a recess 18b similar to the recess 16a of the first piston 16.

The first and second pistons 16, 18, are sealed to the housing 11 by means of a respective sealing 20, such as an O sealing.

Figure 7:
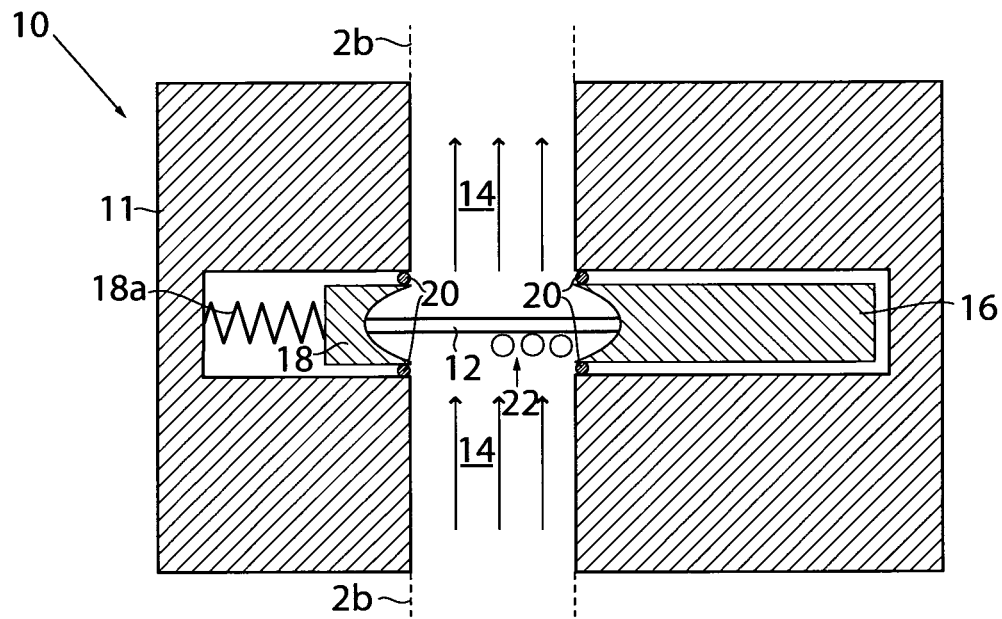
FIG. 7 is a sectional view similar to that of FIG. 4 showing particles before a cleaning operation.

A preferred embodiment of a cleaning method according to the invention will now be described with reference to FIGS. 7-10, showing different operational steps of the above-described device. FIG. 7 is a view similar to that of FIG. 4. However, this figure shows the cleaning device 10 during operation, wherein particles, generally designated 22, have assembled on the filter 12.

Figure 8:
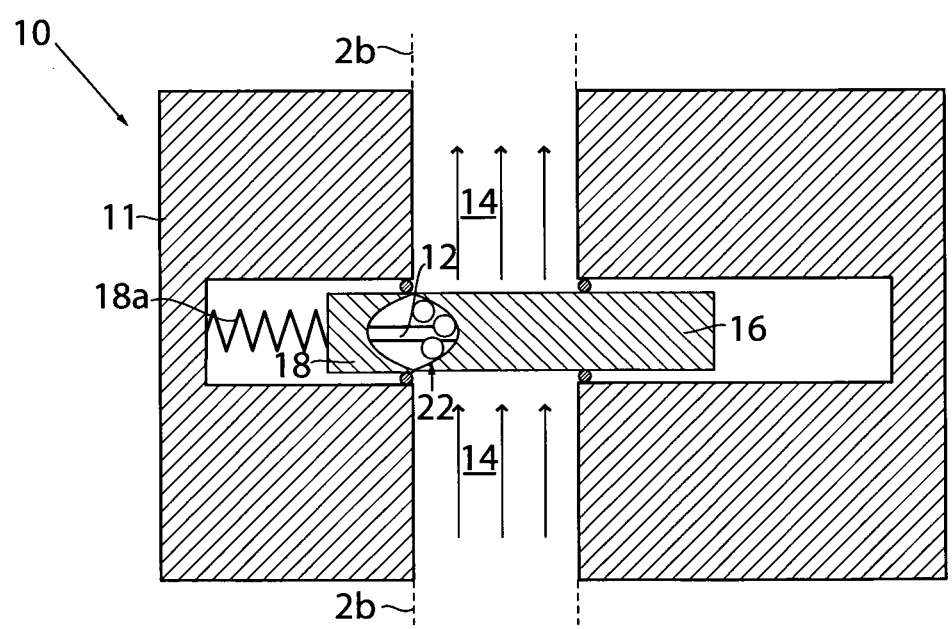
FIG. 8 is a sectional view similar to that of FIG. 4 during a first step of a cleaning operation.

In FIG. 8, the first piston 16 has moved linearly from the retracted starting position shown FIG. 7 to an extended position, wherein the outer end portion thereof is in contact with the second piston 18. Due to the recess 16a in the outer end of the first piston 16, the particles 22 have been assembled in the recess 16a, whereby they have been brought with the first piston 16 during the movement thereof. In the step shown in FIG. 8, the particles are confined in the recess 16a between the first and second pistons 16, 18.

Figure 9:
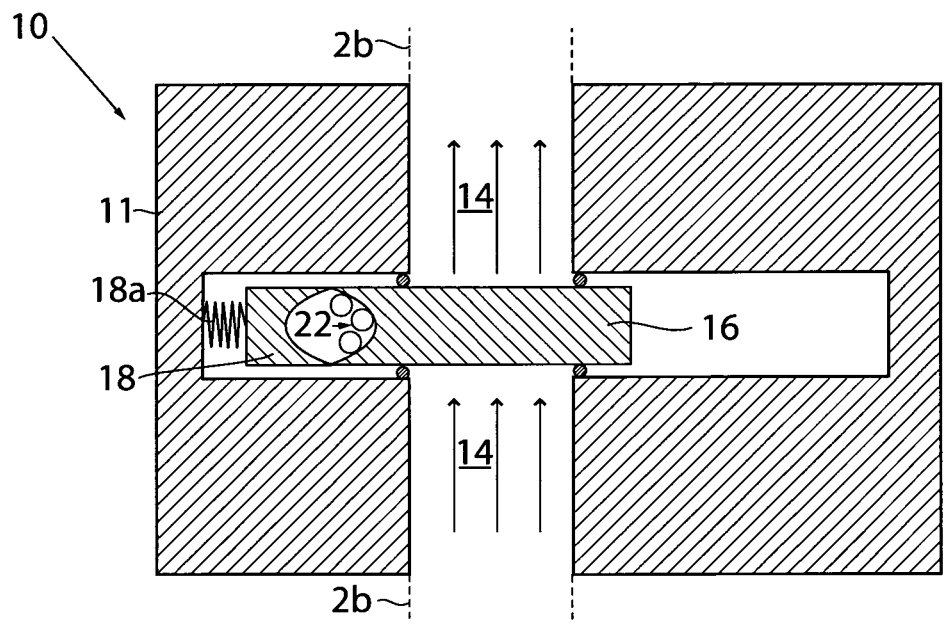
FIG. 9 is a sectional view similar to that of FIG. 4 during a second step of a cleaning operation.

By moving the first piston 16 an additional distance from the position shown in FIG. 8, the second piston 18 is pushed against the force of the spring 18a to a fully retracted position, see FIG. 9. The plurality of strips 12a is in this position fully received in a respective channel 16b in the first piston. It is seen that the outer ends of the first and second pistons define an unobstructed cavity in which the particles are confined. It is thereby possible to remove these by some suitable means. One such means could be a third piston 24, which is movable in a direction perpendicular to both the direction of the flow passageway 14 and the direction of movement of the first and second pistons 16, 18. This third piston, the movement of which could be controlled by means of pressurized air, a solenoid, an electric motor etc., scrapes off the particles collected by the first piston 16 and moves them to a place outside of the cleaning device 10 and the flow passageway 14.

Figure 10:
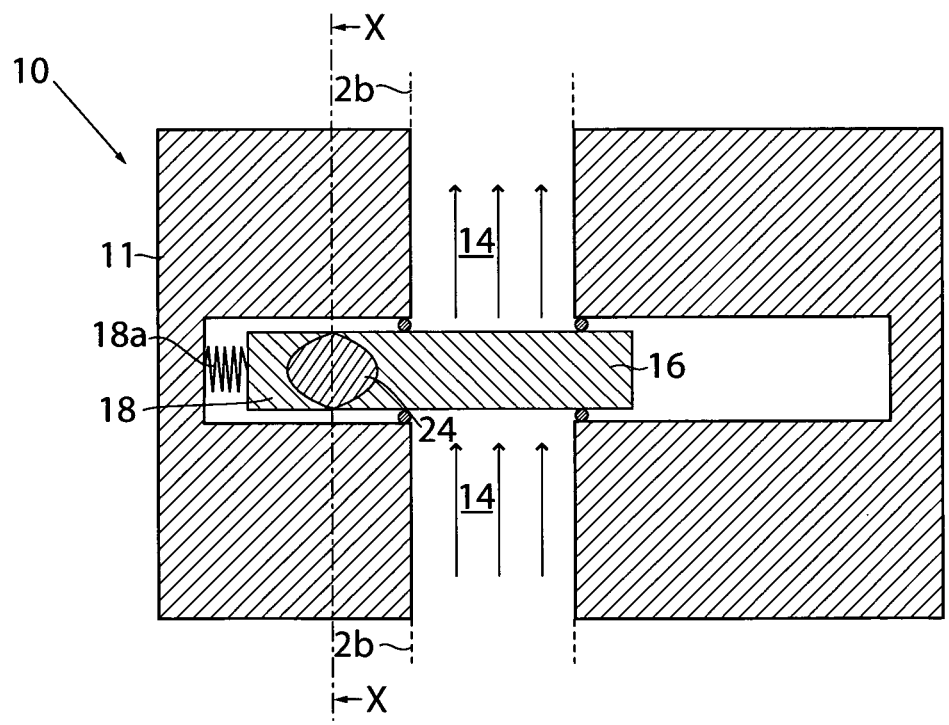
FIG. 10 is a sectional view similar to that of FIG. 4 during a third step of a cleaning operation.
Figure 11:
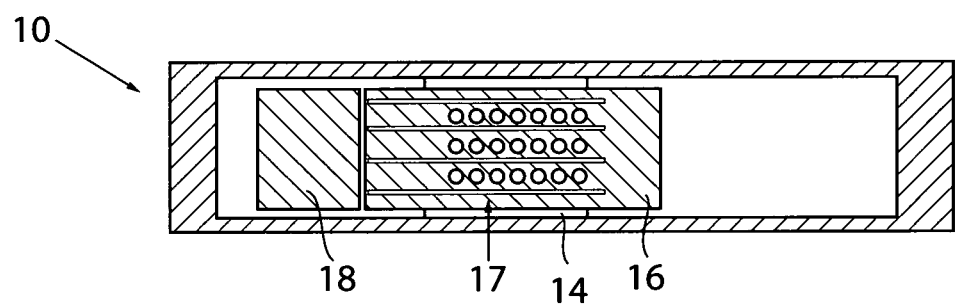
FIG. 11 is a cross sectional view similar to that of FIG. 5 during a cleaning operation.

FIG. 11 shows a side view of the first piston 16 in a fully extended position, i.e., corresponding to the view of FIG. 10. It is here seen that in this position the through holes 17 will be aligned with the flow passageway 14, thereby allowing a flow therethrough also during cleaning of the filter 12.

Figure 12:
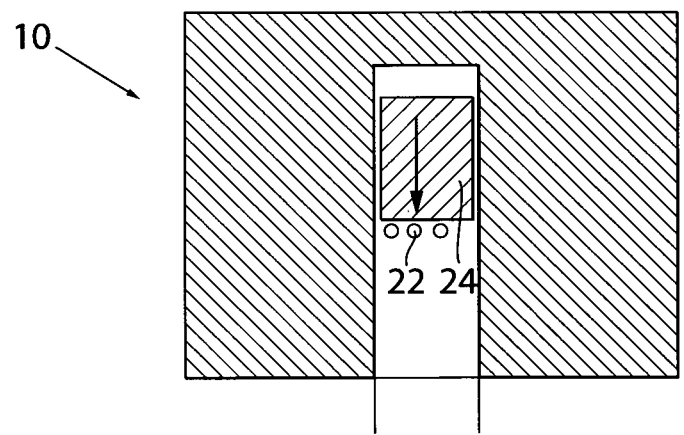
FIG. 12 is a sectional view of the cleaning device of FIG. 10 taken along the line X-X showing a cleaning ejection piston before ejection of particles.
Figure 13:
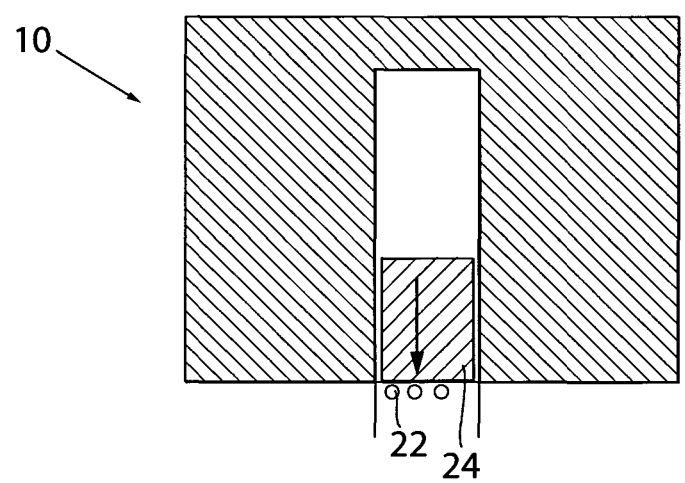
FIG. 13 is a view similar to that of FIG. 11 but after ejection of particles.

FIG. 12 shows a cross-sectional view taken along line X-X of FIG. 10. It is here seen that the third piston 24 collects the particles 22 during a downward movement, indicated by an arrow in the figure. The particles are ejected from the cleaning device 10 when the third piston 24 has reached its lower end position, shown in FIG. 13.

Again with reference to FIG. 9, it will be realized that pressurized air can be used for ejecting the collected particles from the cavity formed by the first piston 16 and the second piston 18.

A cleaning system, generally designated 28 and comprising a cleaning device as described above will now be described with reference to FIGS. 14-26.

A cleaning system is shown in a more generalized block diagram form in FIG. 14, wherein the patient's skin 36, generally shown by a vertical line, separates the interior of the patient to the right of the line from the exterior to the left of the line.

FIG. 15 shows an embodiment of the invention identical to that of FIG. 14, except that a reversing device in the form of an electric switch 38 operable by polarized energy also is implanted in the patient for reversing the cleaning device 10. The wireless remote control of the external energy transmission device 34 transmits a wireless signal that carries polarized energy and the implanted energy transforming device 30 transforms the wireless polarized energy into a polarized current for operating the electric switch 38. When the polarity of the current is shifted by the implanted energy transforming device 30 the electric switch 38 reverses the function performed by the cleaning device 10.

FIG. 16 shows an embodiment of the invention identical to that of FIG. 14, except that an operation device 40 implanted in the patient for regulating the cleaning device 10 is provided between the implanted energy transforming device 30 and the cleaning device 10. This operation device can be in the form of a motor 40, such as an electric servo motor. The motor 40 is powered with energy from the implanted energy transforming device 30, as the remote control of the external energy transmission device 34 transmits a wireless signal to the receiver of the implanted energy transforming device 30.

FIG. 17 shows an embodiment of the invention identical to that of FIG. 14, except that it also comprises an operation device is in the form of an assembly 42 including a motor/pump unit 78 and a fluid reservoir 46 is implanted in the patient. In this case the cleaning device 10 is hydraulically operated, i.e. hydraulic fluid is pumped by the motor/pump unit 44 from the fluid reservoir 46 through a conduit 48 to the cleaning device 10 to operate the cleaning device, and hydraulic fluid is pumped by the motor/pump unit 44 back from the cleaning device 10 to the fluid reservoir 46 to return the cleaning device to a starting position. The implanted energy transforming device 30 transforms wireless energy into a current, for example a polarized current, for powering the motor/pump unit 44 via an electric power supply line 50.

Instead of a hydraulically operated cleaning device 10, it is also envisaged that the operation device comprises a pneumatic operation device. In this case, pressurized air can be used for regulation and the fluid reservoir is replaced by an air chamber and the fluid is replaced by air.

Figure 18:
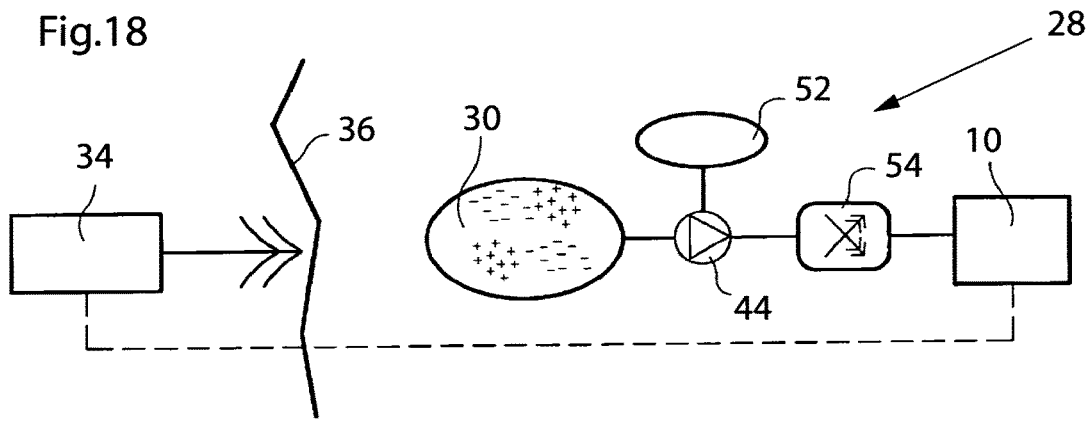

FIG. 18 shows an embodiment of the invention comprising the external energy transmission device 34 with its wireless remote control, the cleaning device 10, in this case hydraulically operated, and the implanted energy transforming device 30, and further comprising a hydraulic fluid reservoir 52, a motor/pump unit 44 and an reversing device in the form of a hydraulic valve shifting device 54, all implanted in the patient. The motor of the motor/pump unit 44 is an electric motor. In response to a control signal from the wireless remote control of the external energy transmission device 34, the implanted energy transforming device 30 powers the motor/pump unit 44 with energy from the energy carried by the control signal, whereby the motor/pump unit 44 distributes hydraulic fluid between the hydraulic fluid reservoir 52 and the cleaning device 10. The remote control of the external energy transmission device 34 controls the hydraulic valve shifting device 54 to shift the hydraulic fluid flow direction between one direction in which the fluid is pumped by the motor/pump unit 44 from the hydraulic fluid reservoir 52 to the cleaning device 10 to operate the cleaning device, and another opposite direction in which the fluid is pumped by the motor/pump unit 44 back from the cleaning device 10 to the hydraulic fluid reservoir 52 to return the cleaning device to a starting position.

Figure 19:
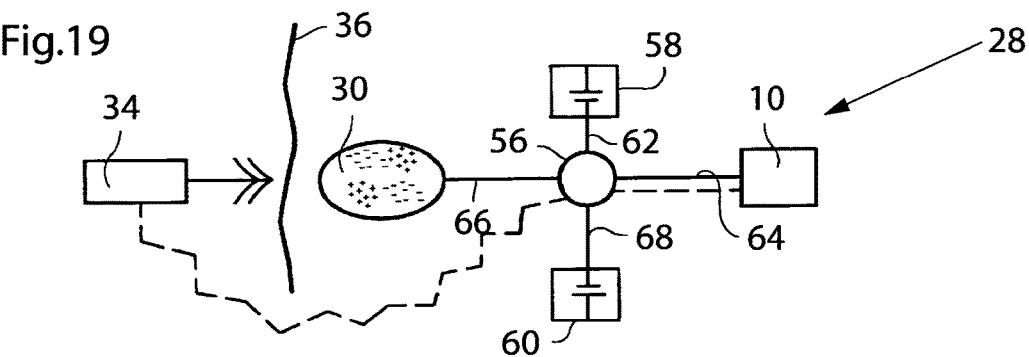

FIG. 19 shows an embodiment of the invention identical to that of FIG. 14, except that an internal control unit 56 controlled by the wireless remote control of the external energy transmission device 34, an accumulator 58 and a capacitor 60 also are implanted in the patient. The internal control unit 56 arranges storage of electric energy received from the implanted energy transforming device 30 in the accumulator 58, which supplies energy to the cleaning device 10. In response to a control signal from the wireless remote control of the external energy transmission device 34, the internal control unit 56 either releases electric energy from the accumulator 58 and transforms the released energy via power lines 62 and 64, or directly transforms electric energy from the implanted energy transforming device 30 via a power line 66, the capacitor 60, which stabilizes the electric current, a power line 68 and the power line 64, for the operation of the cleaning device 10.

The internal control unit is preferably programmable from outside the patient's body. In a preferred embodiment, the internal control unit is programmed to regulate the cleaning device 10 to remove any particles from the fluid movement device and place the particles outside the fluid movement device repeatedly according to a pre-programmed time-schedule.

In accordance with an alternative, the capacitor 60 in the embodiment of FIG. 19 may be omitted. In accordance with another alternative, the accumulator 58 in this embodiment may be omitted.

Figure 20:
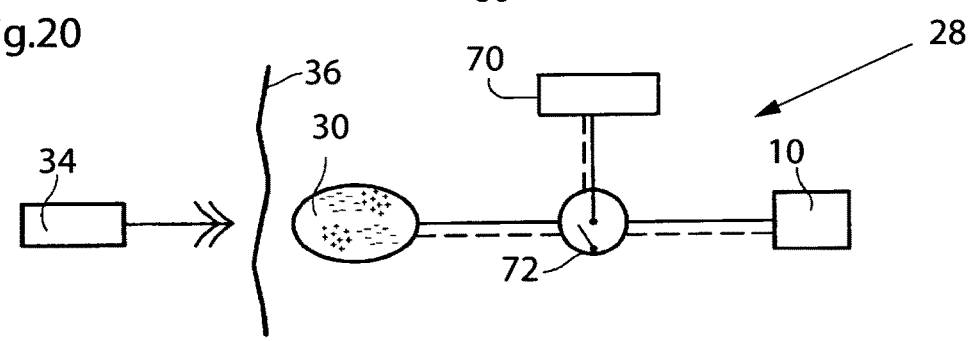

FIG. 20 shows an embodiment of the invention identical to that of FIG. 14, except that a battery 70 for supplying energy for the operation of the cleaning device 10 and an electric switch 72 for switching the operation of the cleaning device 10 also are implanted in the patient. The electric switch 72 is operated by the energy supplied by the implanted energy transforming device 30 to switch from an off mode, in which the battery 70 is not in use, to an on mode, in which the battery 70 supplies energy for the operation of the cleaning device 10.

Figure 21:
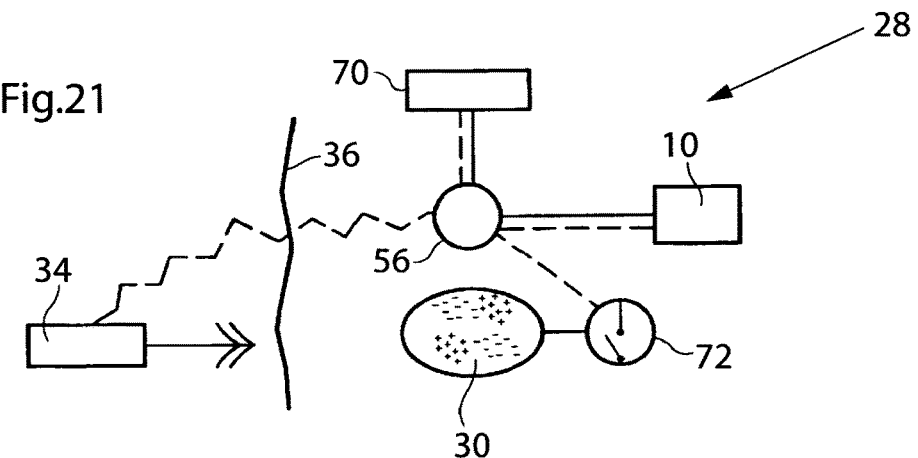

FIG. 21 shows an embodiment of the invention identical to that of FIG. 20, except that an internal control unit 56 controllable by the wireless remote control of the external energy transmission device 34 also is implanted in the patient. In this case, the electric switch 72 is operated by the energy supplied by the implanted energy transforming device 30 to switch from an off mode, in which the wireless remote control is prevented from controlling the internal control unit 56 and the battery is not in use, to a standby mode, in which the remote control is permitted to control the internal control unit 56 to release electric energy from the battery 70 for the operation of the cleaning device 10.

Figure 22:
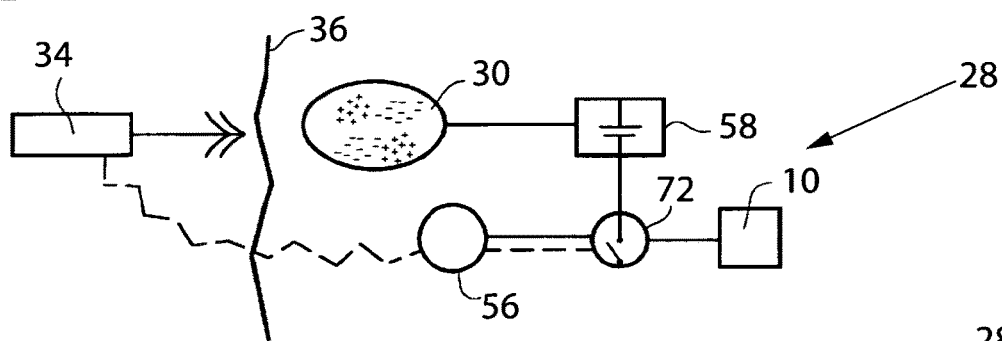

FIG. 22 shows an embodiment of the invention identical to that of FIG. 21, except that an accumulator 58 is substituted for the battery 70 and the implanted components are interconnected differently. In this case, the accumulator 58 stores energy from the implanted energy transforming device 30. In response to a control signal from the wireless remote control of the external energy transmission device 34, the internal control unit 56 controls the electric switch 72 to switch from an off mode, in which the accumulator 58 is not in use, to an on mode, in which the accumulator 58 supplies energy for the operation of the cleaning device 10.

Figure 23:
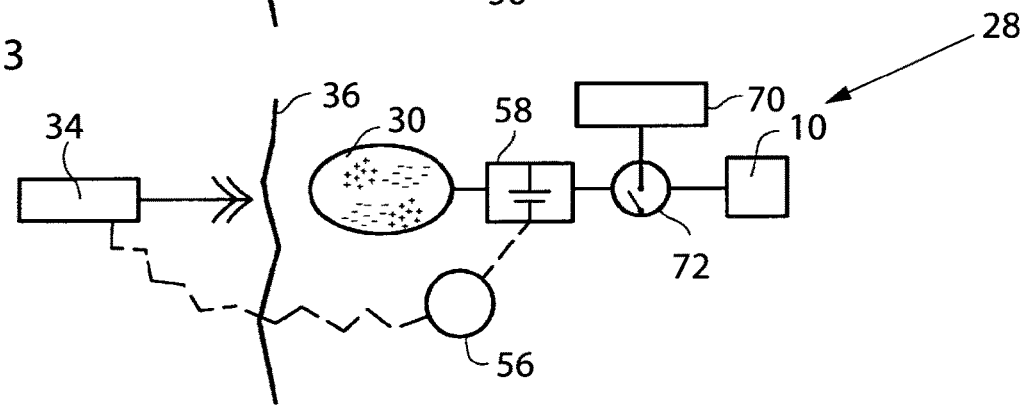

FIG. 23 shows an embodiment of the invention identical to that of FIG. 22, except that a battery 70 also is implanted in the patient and the implanted components are interconnected differently. In response to a control signal from the wireless remote control of the external energy transmission device 34, the internal control unit 56 controls the accumulator 58 to deliver energy for operating the electric switch 72 to switch from an off mode, in which the battery 70 is not in use, to an on mode, in which the battery 70 supplies electric energy for the operation of the cleaning device 10.

Alternatively, the electric switch 72 may be operated by energy supplied by the accumulator 58 to switch from an off mode, in which the wireless remote control is prevented from controlling the battery 70 to supply electric energy and is not in use, to a standby mode, in which the wireless remote control is permitted to control the battery 70 to supply electric energy for the operation of the cleaning device 10.

Figure 24:
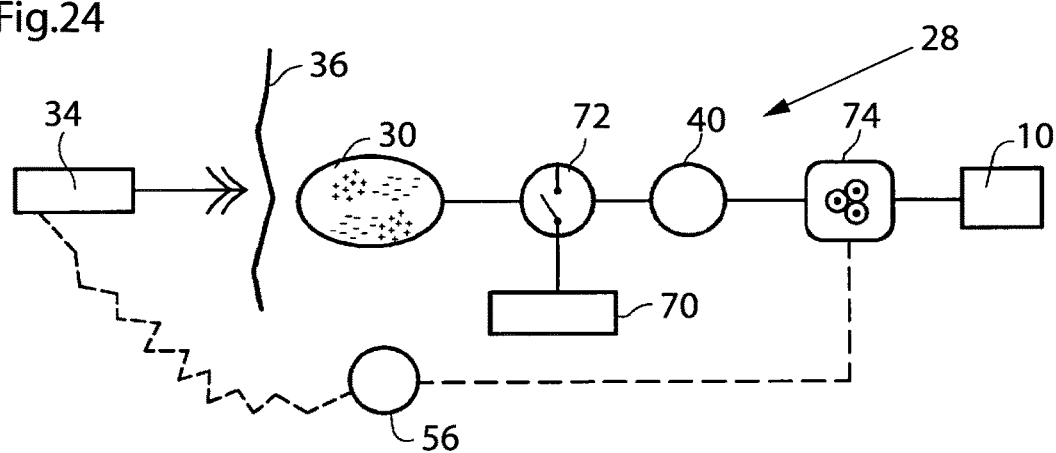

FIG. 24 shows an embodiment of the invention identical to that of FIG. 20, except that a motor 40, a mechanical reversing device in the form of a gear box 74, and an internal control unit 56 for controlling the gear box 74 also are implanted in the patient. The internal control unit 56 controls the gear box 74 to reverse the function performed by the cleaning device 10 (mechanically operated).

Figure 25:
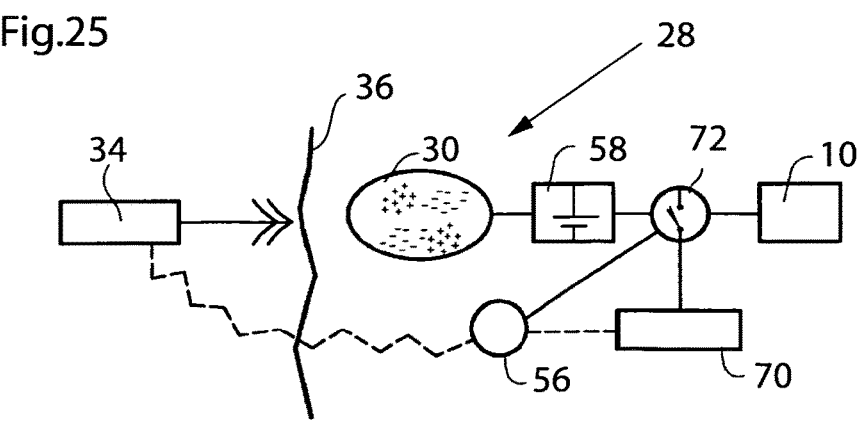

FIG. 25 shows an embodiment of the invention identical to that of FIG. 23 except that the implanted components are interconnected differently. Thus, in this case the internal control unit 56 is powered by the battery 70 when the accumulator 58, suitably a capacitor, activates the electric switch 72 to switch to an on mode. When the electric switch 72 is in its on mode the internal control unit 56 is permitted to control the battery 70 to supply, or not supply, energy for the operation of the cleaning device 10.

Figure 26:
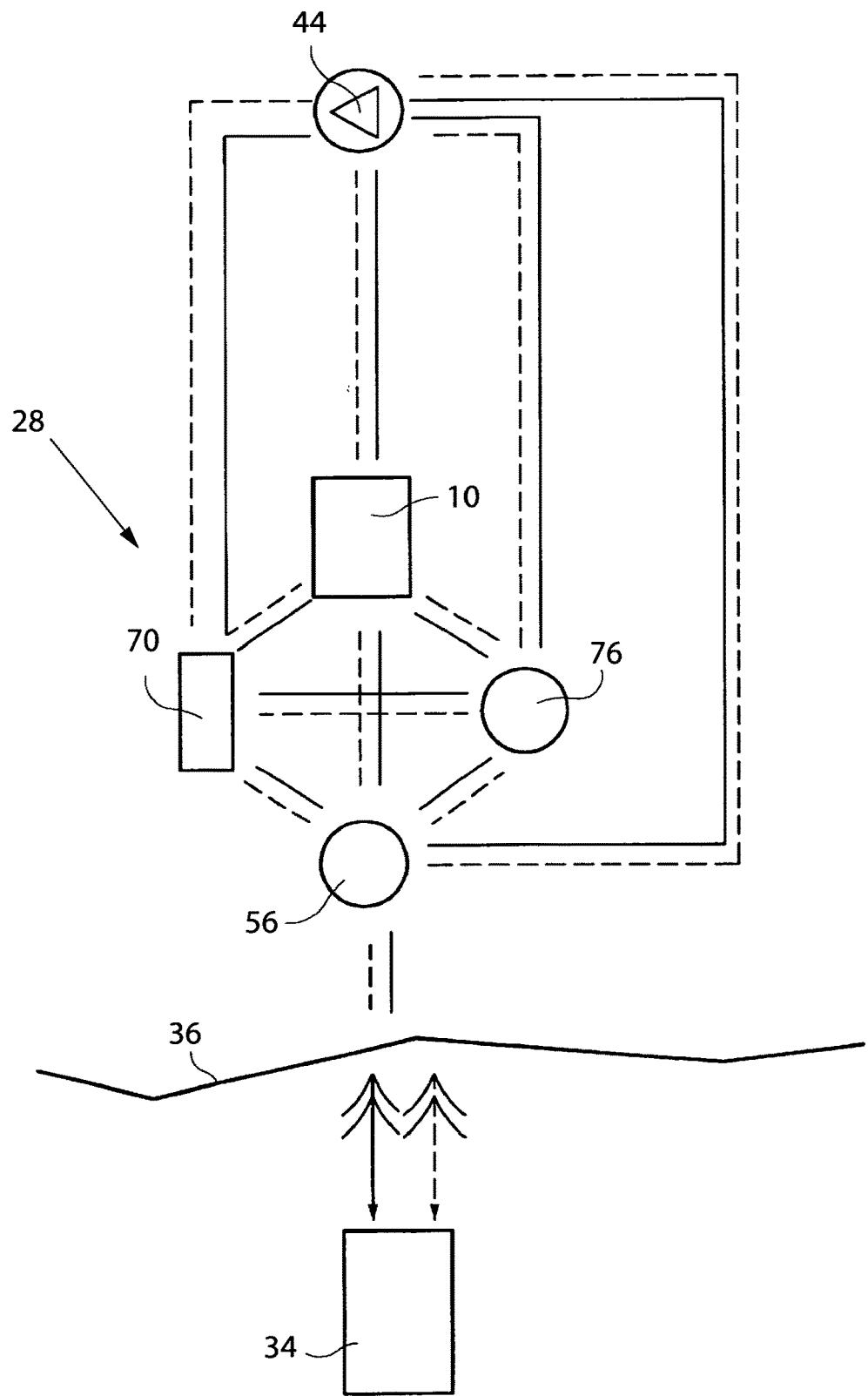

FIG. 26 schematically shows conceivable combinations of implanted components of the apparatus for achieving various communication options. Basically, there are the cleaning device 10, the internal control unit 56, motor/pump unit 44, and the external energy transmission device 34 including the external wireless remote control. As already described above the wireless remote control transmits a control signal which is received by the internal control unit 56, which in turn controls the various implanted components of the apparatus.

A feedback device, preferably in the form of a sensor 76, may be implanted in the patient for sensing a physical parameter of the patient, such as the pressure in a blood vessel. The internal control unit 56, or alternatively the external wireless remote control of the external energy transmission device 34, may control the cleaning device 10 in response to signals from the sensor 76. A transceiver may be combined with the sensor 76 for sending information on the sensed physical parameter to the external wireless remote control. The wireless remote control may comprise a signal transmitter or transceiver and the internal control unit 56 may comprise a signal receiver or transceiver. Alternatively, the wireless remote control may comprise a signal receiver or transceiver and the internal control unit 56 may comprise a signal transmitter or transceiver. The above transceivers, transmitters and receivers may be used for sending information or data related to the cleaning device 10 from inside the patient's body to the outside thereof.

Alternatively, the sensor 76 may be arranged to sense a functional parameter of the cleaning device 10.

Where the motor/pump unit 44 and battery 70 for powering the motor/pump unit 44 are implanted, the battery 70 may be equipped with a transceiver for sending information on the condition of the battery 70.

Figure 27:
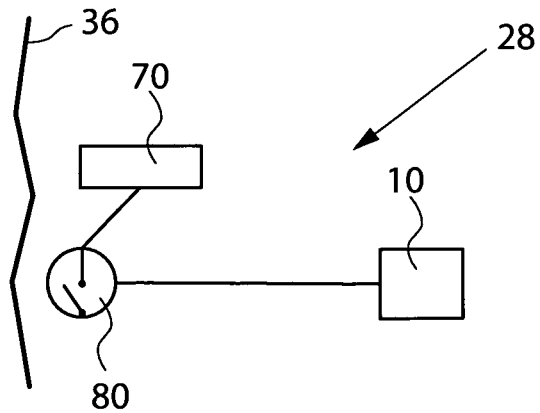

FIG. 27 shows an alternative embodiment wherein the cleaning device 10 is regulated from outside the patient's body. The cleaning system 28 comprises a cleaning device 10 connected to a battery 70 via a subcutaneous switch 80.

Thus, the regulation of the cleaning device 10 is performed non-invasively by manually pressing the subcutaneous switch, whereby the operation of the cleaning device 10 is switched on and off. It will be appreciated that the shown embodiment is a simplification and that additional components, such as an internal control unit, can be added to the cleaning system.

Figure 28:
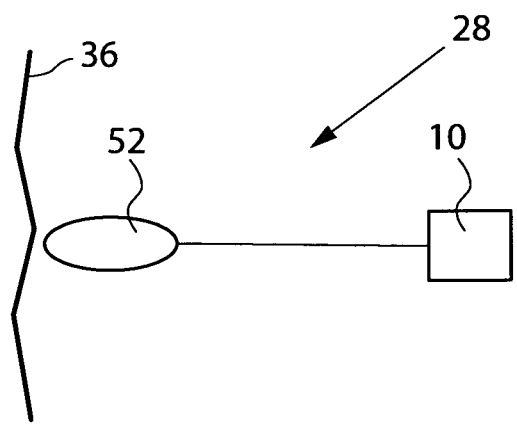

FIG. 28 shows an alternative embodiment, wherein the cleaning system 28 comprises a cleaning device 10 in fluid connection with a hydraulic fluid reservoir 52. Non-invasive regulation is performed by manually pressing the hydraulic reservoir connected to the cleaning device 10.

A further embodiment of a system according to the invention comprises a feedback device for sending information from inside the patient's body to the outside thereof to give feedback information related to at least one functional parameter of the clot removal device or system or a physical parameter of the patient, thereby optimizing the performance of the system.

One preferred functional parameter of the device is correlated to the transfer of energy for charging the internal energy source.

Figure 29:
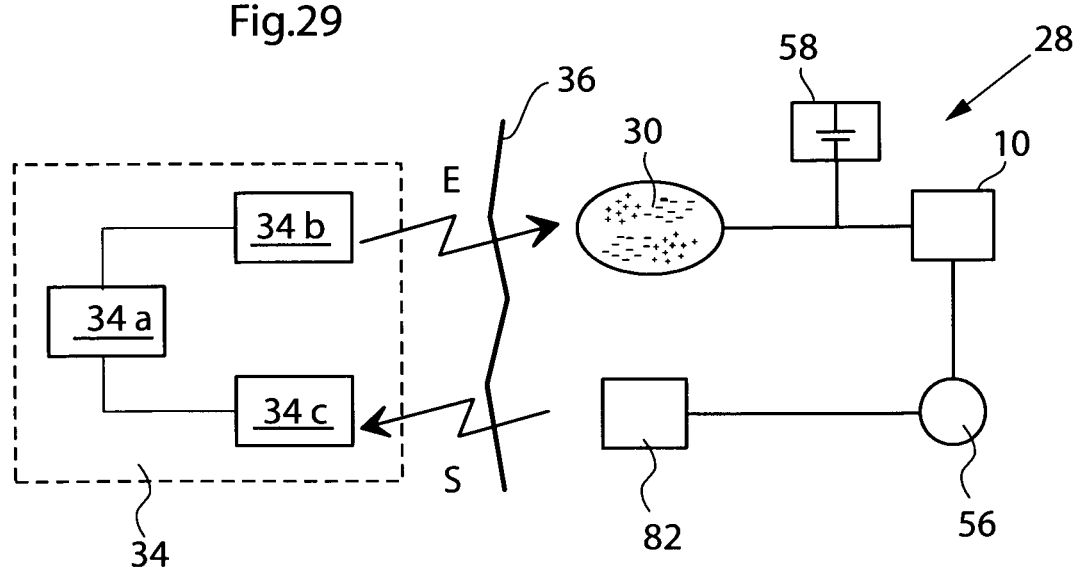

In FIG. 29, an arrangement is schematically illustrated for supplying an accurate amount of energy to a cleaning system 28 implanted in a patient, whose skin 36 is indicated by a vertical line. A cleaning device 10 is connected to an implanted energy transforming device 30, likewise located inside the patient, preferably just beneath the patient's skin 36. Generally speaking, the implanted energy transforming device 30 may be placed in the abdomen, thorax, muscle fascia (e.g. in the abdominal wall), subcutaneously, or at any other suitable location. The implanted energy transforming device 30 is adapted to receive wireless energy E transmitted from an external energy source 34a provided in the external energy transmission device 34 located outside the patient's skin 36 in the vicinity of the implanted energy transforming device 30.

As is well known in the art, the wireless energy E may generally be transferred by means of any suitable Transcutaneous Energy Transfer (TET) device, such as a device including a primary coil arranged in the external energy source 34a and an adjacent secondary coil arranged in the implanted energy transforming device 30. When an electric current is fed through the primary coil, energy in the form of a voltage is induced in the secondary coil which can be used to operate a cleaning device, e.g. after storing the incoming energy in an energy storing device or accumulator, such as a battery or a capacitor. However, the present invention is generally not limited to any particular energy transfer technique, TET devices or energy storing devices, and any kind of wireless energy may be used. Other energy transfer methods include but are not limited to non-induction methods such as by means of ultra-sonic devices or using light.

The amount of transferred energy can be regulated by means of an external control unit 34b controlling the external energy source 34a based on the determined energy balance, as described above. In order to transfer the correct amount of energy, the energy balance and the required amount of energy can be determined by means of an internal control unit 56 connected to the cleaning device 10. The internal control unit 56 may thus be arranged to receive various measurements obtained by suitable sensors or the like, not shown, measuring certain characteristics of the cleaning device 10, reflecting the required amount of energy needed for proper operation of the cleaning device 10. Moreover, the current condition of the patient may also be detected by means of suitable measuring devices or sensors, in order to provide parameters reflecting the patient's condition. Hence, such characteristics and/or parameters may be related to the current state of the cleaning device 10, such as power consumption, operational mode and temperature, as well as the patient's condition reflected by, e.g., body temperature, blood pressure, heartbeats and breathing.

Furthermore, an energy storing device or accumulator 58 may optionally be connected to the implanted energy transforming device 30 for accumulating received energy for later use by the cleaning device 10. Alternatively or additionally, characteristics of such an accumulator, also reflecting the required amount of energy, may be measured as well. The accumulator may be replaced by a battery, and the measured characteristics may be related to the current state of the battery, such as voltage, temperature, etc. In order to provide sufficient voltage and current to the cleaning device 10, and also to avoid excessive heating, it is clearly understood that the battery should be charged optimally by receiving a correct amount of energy from the implanted energy transforming device 30, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 56. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 56 is adapted to determine the energy balance and/or the currently required amount of energy, (either energy per time unit or accumulated energy) based on measurements made by the above-mentioned sensors or measuring devices on the cleaning device 10, or the patient, or an energy storing device if used, or any combination thereof. The internal control unit 56 is further connected to an internal signal transmitter 82, arranged to transmit a control signal reflecting the determined required amount of energy, to an external signal receiver 34c connected to the external control unit 34b. The amount of energy transmitted from the external energy source 34a may then be regulated in response to the received control signal.

Alternatively, sensor measurements can be transmitted directly to the external control unit 34b wherein the energy balance and/or the currently required amount of energy can be determined by the external control unit 34b, thus integrating the above-described function of the internal control unit 56 in the external control unit 34b. In that case, the internal control unit 56 can be omitted and the sensor measurements are supplied directly to the internal signal transmitter 82 which sends the measurements over to the external signal receiver 34c and the external control unit 34b. The energy balance and the currently required amount of energy can then be determined by the external control unit 34b based on those sensor measurements.

Hence, feedback of information indicating the required energy can be used, which is more efficient because it is based on the actual use of energy that is compared to for example the received energy, e.g. with respect to the amount of energy, the energy difference, or the energy receiving rate as compared to the energy rate used by the cleaning device. The cleaning device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the clot removal device.

The internal signal transmitter 82 and the external signal receiver 34c may be implemented as separate units using suitable signal transfer means, such as radio, IR (Infrared) or ultrasonic signals. Alternatively, the internal signal transmitter 82 and the external signal receiver 34c may be integrated in the implanted energy transforming device 30 and the external energy source 34a, respectively, so as to convey control signals in a reverse direction relative to the energy transfer, basically using the same transmission technique. The control signals may be modulated with respect to frequency, phase or amplitude.

The energy supply arrangement illustrated in FIG. 29 may operate basically in the following manner. The energy balance is first determined by the internal control unit 56. A control signal reflecting the required amount of energy is also created by the internal control unit 56, and the control signal is transmitted from the internal signal transmitter 82 to the external signal receiver 34c. Alternatively, the energy balance can be determined by the external control unit 34b instead depending on the implementation, as mentioned above. In that case, the control signal may carry measurement results from various sensors. The amount of energy emitted from the external energy source 34a can then be regulated by the external control unit 34b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 34a, such as voltage, current, amplitude, wave frequency and pulse characteristics.

A method is thus provided for controlling transmission of wireless energy supplied to an electrically operable cleaning device implanted in a patient. The wireless energy E is transmitted from an external energy source located outside the patient and is received by an internal energy receiver located inside the patient, the internal energy receiver being connected to the clot removal device for directly or indirectly supplying received energy thereto. An energy balance is determined between the energy received by the internal energy receiver and the energy used for the cleaning device. The transmission of wireless energy E from the external energy source is then controlled based on the determined energy balance.

A system is also provided for controlling transmission of wireless energy supplied to an electrically operable cleaning device implanted in a patient. The system is adapted to transmit the wireless energy E from an external energy source located outside the patient which is received by an implanted energy transforming device located inside the patient, the implanted energy transforming device being connected to the cleaning device for directly or indirectly supplying received energy thereto. The system is further adapted to determine an energy balance between the energy received by the implanted energy transforming device and the energy used for the cleaning device, and control the transmission of wireless energy E from the external energy source, based on the determined energy balance.

The functional parameter of the device is correlated to the transfer of energy for charging the internal energy source.

In yet an alternative embodiment, the external source of energy is controlled from outside the patient's body to release electromagnetic wireless energy, and released electromagnetic wireless energy is used for operating the cleaning device.

In another embodiment, the external source of energy is controlling from outside the patient's body to release non-magnetic wireless energy, and released non-magnetic wireless energy is used for operating the cleaning device.

Those skilled in the art will realize that the above various embodiments according to FIGS. 14-30 could be combined in many different ways. For example, the electric switch 38 operated polarized energy could be incorporated in any of the embodiments of FIGS. 16, 19-25, the hydraulic valve shifting device 54 could be incorporated in the embodiment of FIG. 17, and the gear box 74 could be incorporated in the embodiment of FIG. 16.

Figure 30:
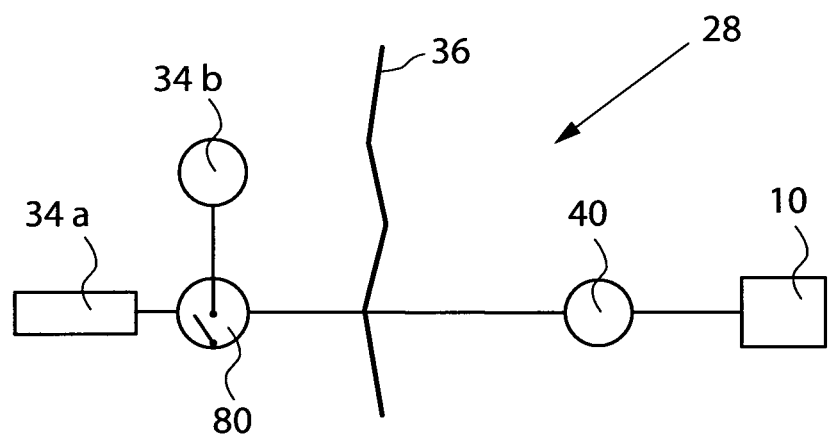

Wireless transfer of energy for operating the cleaning device has been described to enable non-invasive operation. It will be appreciated that the cleaning device can be operated with wire bound energy as well. One such example is shown in FIG. 30, wherein an external switch 84 is interconnected between the external energy source 34a and an operation device, such as an electric motor regulating the cleaning device 10, by means of power lines 86 and 88. An external control unit 34b controls the operation of the external switch to effect proper operation of the cleaning device 10.

Figure 31:
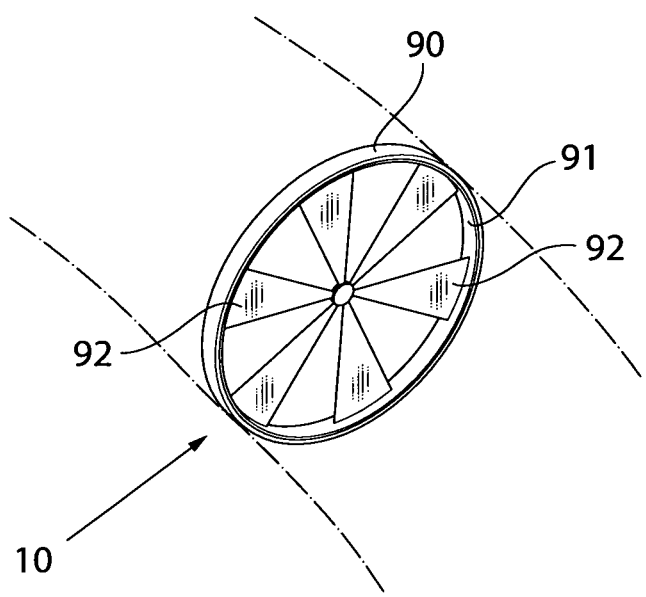
FIG. 31 is a view of an alternative embodiment of a cleaning system.

Also other filters can be used in the cleaning device 10. One such filter is depicted in FIG. 31. The filter 90 in FIG. 31 comprises a rotating member 91 located in the flow passage way of the fluid movement device. The rotating member can be formed by a number of segments 92. Particles in the flow will caught by the segments and moved to the rim of the rotating member 91 where the particles can be effectively removed from the flow pathway of the fluid movement device. The cleaning device in FIG. 31 can be powered in the same manner as the cleaning device described above.

Figure 32:
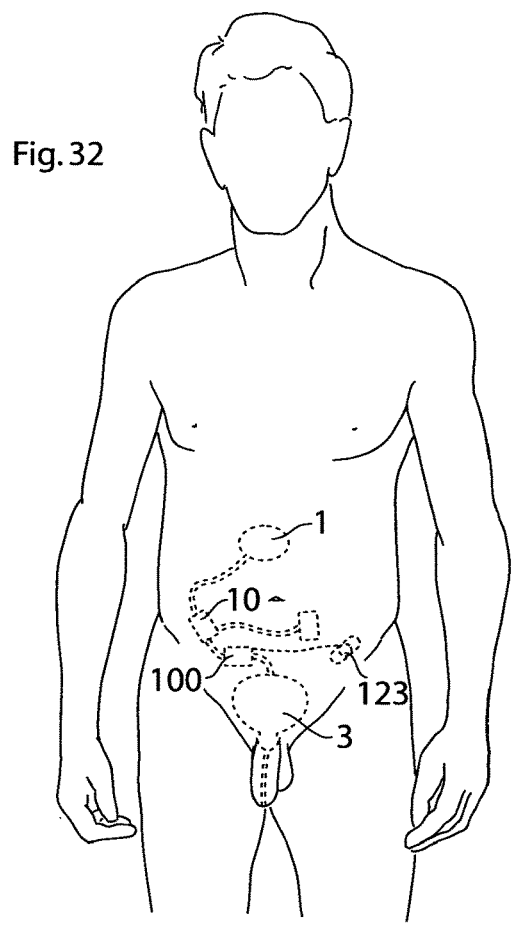
FIG. 32 is a general view of an implanted drainage system in a patient.

In FIG. 32 a general view of a patient having an implanted drainage system as described herein. The system comprises a first end of the drainage system located in a treatment area 1. The system further comprises a pump 100 adapted to move fluid from the treatment area 1 to a delivery area 3. The treatment area can be any area from which fluid is to be move including but not limited to the abdomen, the lungs and the brain. Similarly the delivery area can be any suitable delivery area within the body, including but not limited to the Urine bladder and the stomach.

The pump can be powered by an energy source 123 as described above. The energy source can be energized from outside the patient using a wireless energy transfer device. The energy transfer device can transfer energy in a way suitable such as by inductive energy using coils or ultra sonic energy transfer or by transmitting light through the skin of the patient. Also the fluid passageway from the treatment area to the delivery area can comprise a cleaning device 10 as described above. The cleaning device can in one embodiment be powered by a motor and the motor can then be supplied with energy from the energy source 123.

Figure 33:
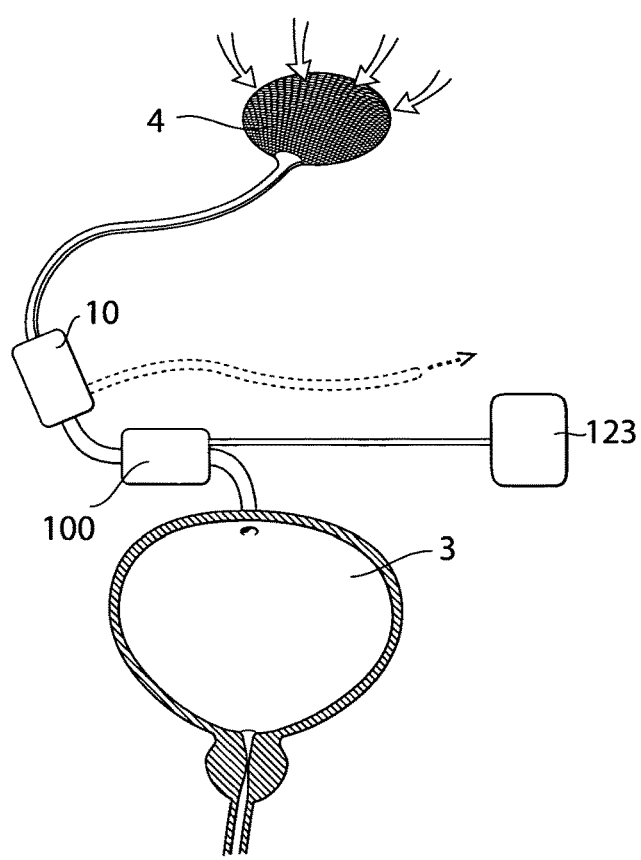
FIG. 33 is a detailed view of a drainage system.

In FIG. 33 the drainage system is shown in more detail. The view in FIG. 33 corresponds to the view in FIG. 32. However instead of showing the treatment area 1, FIG. 33 shows and end member 4 of the tube located in the treatment area. As described above the end member 4 can be designed differently for different treatment areas. Different end members are described in more detail below.

Figure 34A:
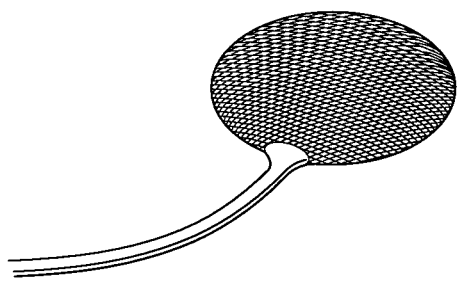
FIGS. 34a-34d are views of exemplary designs of tube ends for different treatment areas.
Figure 34B:
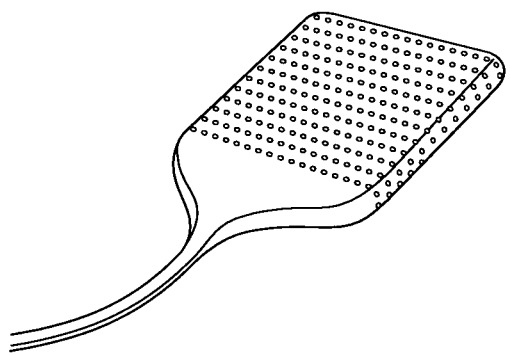

In FIGS. 34a-34d different exemplary designs of end members 4 are shown in more detail. Thus, a connecting tube for use in an implantable fluid movement device being adapted to move body fluid from one part of the body, herein termed treatment area, of a human or mammal patient is provided. A distal end of the connecting tube comprises in accordance with one embodiment a portion having a flat shape. Such an end portion can advantageously be used in the lungs when moving fluid from the lungs. The end portion can have an essential circular shape as is shown in FIG. 34a or have a polygonal shape as is shown in FIG. 34b.

Figure 34C:
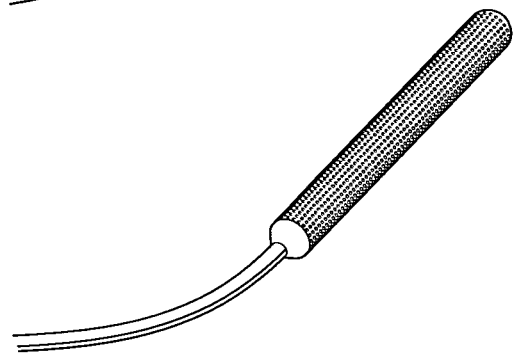
Figure 34D:
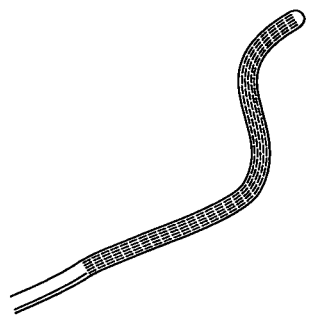

In accordance with one embodiment the distal end of the connecting tube can comprises a portion having a generally cylindrical shape as is shown in FIG. 34c. Such a shape can be preferred in applications where there is a risk that the tube end is sucked towards the wall of the treatment area. In FIG. 34d yet another embodiment is shown with a very flexible tube end that can be used as a versatile tube in that it combines advantages of a flat tube end and a cylindrical tube end at the expense of the disadvantages of being flexible.

The tube ends are provided with holes or formed by a netlike structure. The diameter of the hole can in accordance with one embodiment be in the range of 1-10 mm. The number of holes and the diameter can typically depend on the treatment. As a general rule more holes and larger holes will give a lower sucking force and vice versa. Thus, areas where a low sucking force is required such as in the lungs can be treated using a tube end having many and large holes in the tube end.

Figure 35:
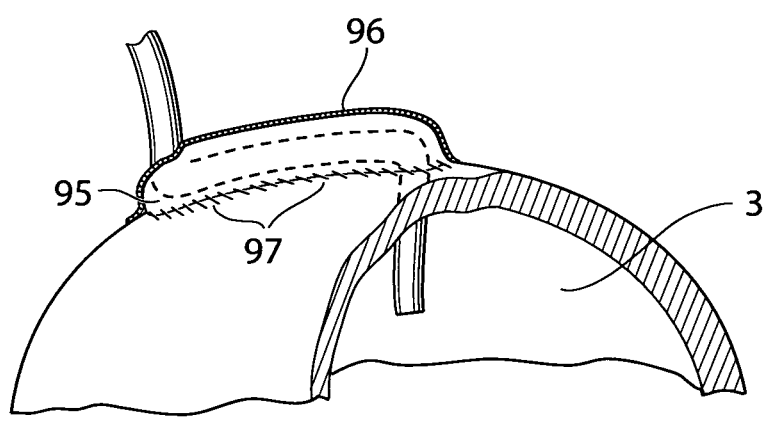
FIG. 35 is a view of a securing arrangement for securing a tube end in a bladder, such as the urine bladder.
Figure 36A:
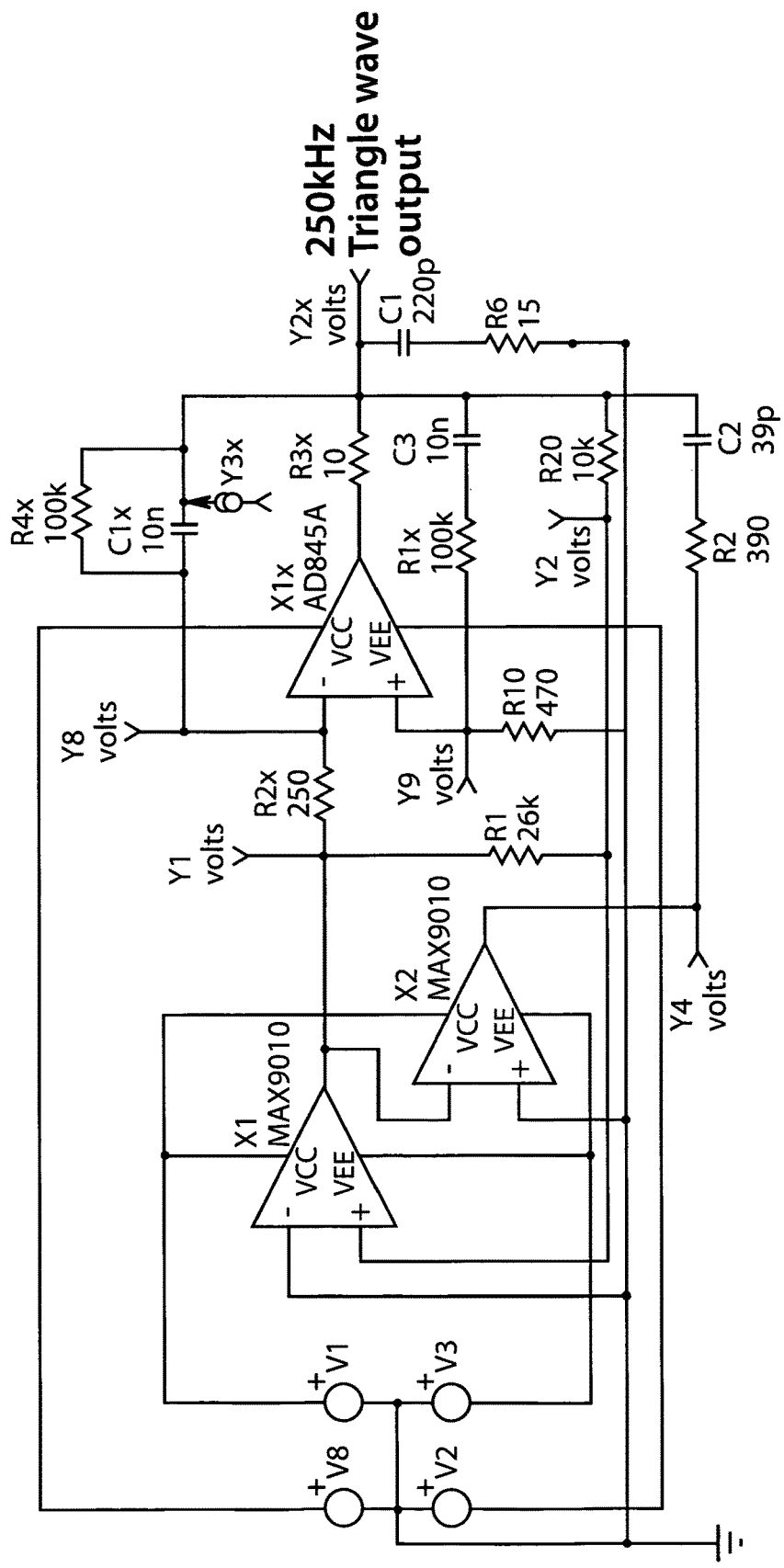
FIG. 36a is a circuit diagram showing an energy transfer amplifier, where the energy is transferred by ultrasonic waves.
Figure 36B:
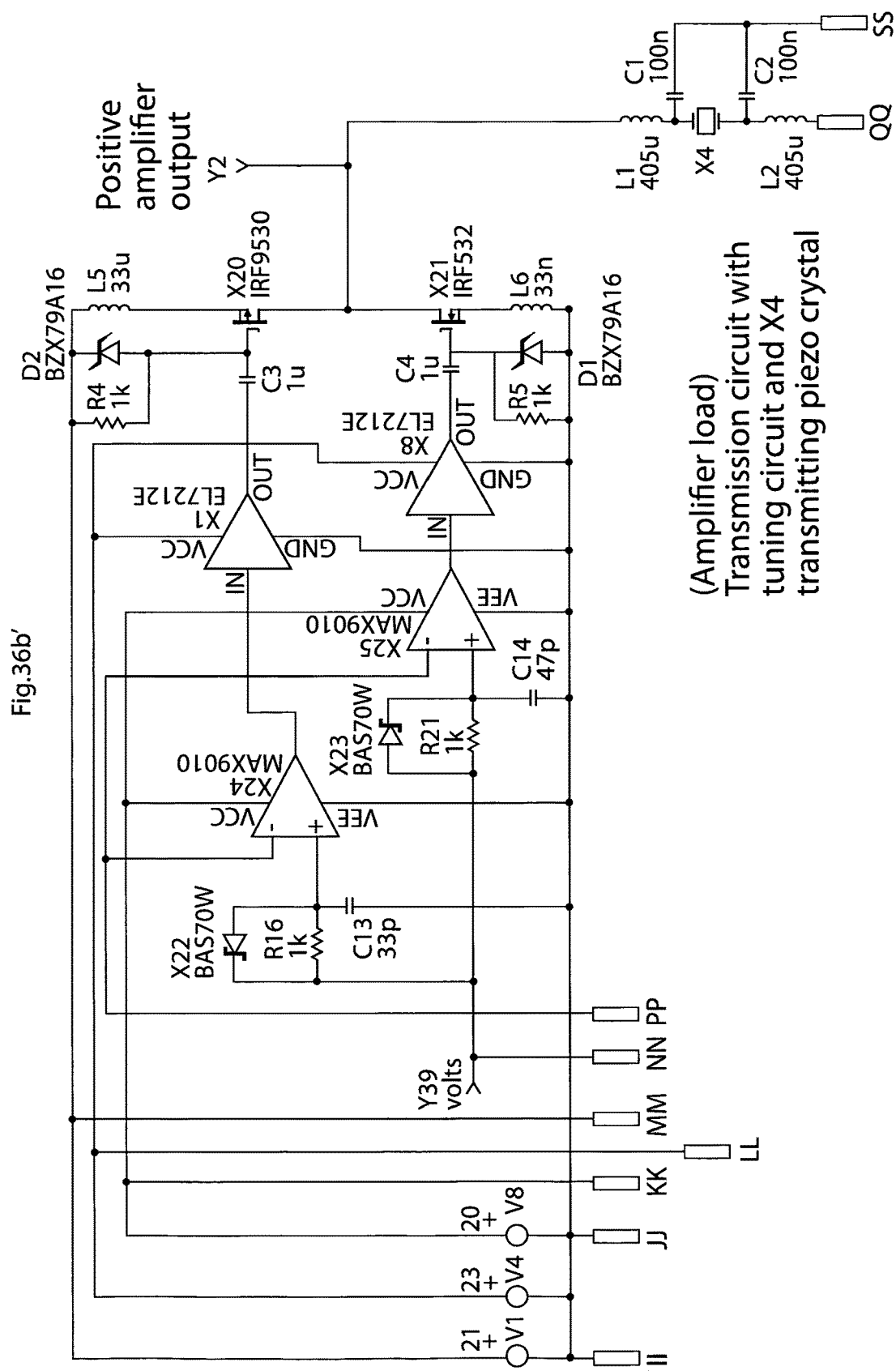
FIG. 36b is a circuit diagram showing further another embodiment of an amplifier.

In FIG. 35 a securing arrangement for securing a second end of a tube of the fluid movement device into the urine bladder is depicted. The arrangement comprises a tube end placed in the urine bladder 3 through a hole made in the wall of the urine bladder. On the outside the tube is led through a tunnel 95 formed by folding the outside wall of the urine bladder around the tube. The tunnel is secured around the tube by sutures 97 or similar. At the end of the tunnel a net structure 96 is tightly secured to the tube. The net structure has small diameter typically smaller than 0.5 mm. In any event the net structure has holes that will be small enough to be overgrown by tissue thereby providing a tight sealing so that no leakage occur. As stated above energy can be transferred in different manners from outside a patient into a implanted drain as described herein. In particular the energy can be transferred by means of an inductive energy transfer or by transmission using an ultrasonic energy transmission, or by transmission of energy using light. In FIG. 36a a triangle wave generator circuit which output is connected as an input terminal of an amplifier used for transmitting energy using an ultrasonic energy transmission. In FIGS. 36a and 36b the symbols Y1, Y2, Y3 and so on symbolize test points within the circuit. The components in the circuit diagrams and their respective values are values that work in this particular implementation which of course is only one of an infinite number of possible design solutions.

Figure 36C:
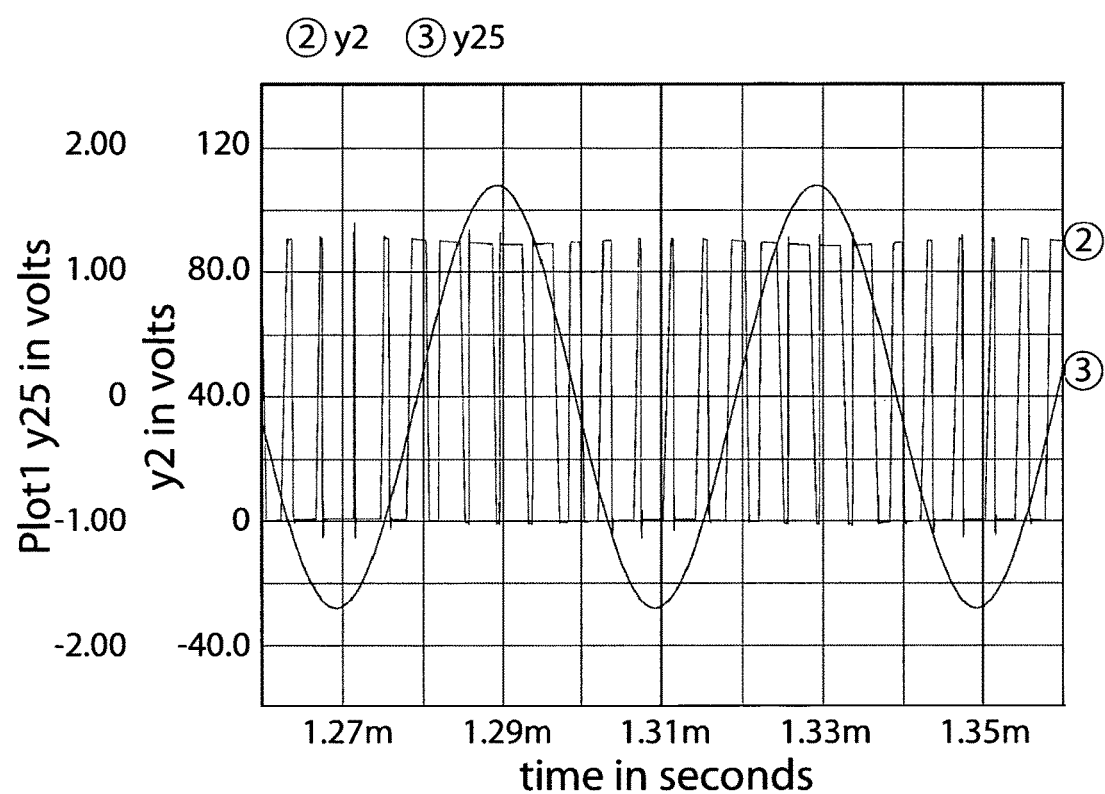

FIG. 36a shows a circuit diagram containing most of an exemplary amplifier, in the lower left corner of FIG. 36a there is the LF input which is the input for the 25 kHz sine wave that should be amplified into a digital output signal. The LF-input there is the triangle wave input emanating from the Triangle schematic. To the right in the middle in the Core schematic there is the transmitting crystal, X4, connected to the differential digital outputs, positive and negative output, of the amplifier. The transmitting crystal X4 is in series with its associated tuning circuit components tuned to the sending frequency, which in this particular case is 25 kHz. FIGS. 36c-36d displays the relationship between the input and the output signal of the amplifier, in FIG. 36c Y25 is the input signal and Y2 is the positive digital output signal from the amplifier and in FIG. 36d Y13 is the negative digital output from the amplifier.

Figure 37:
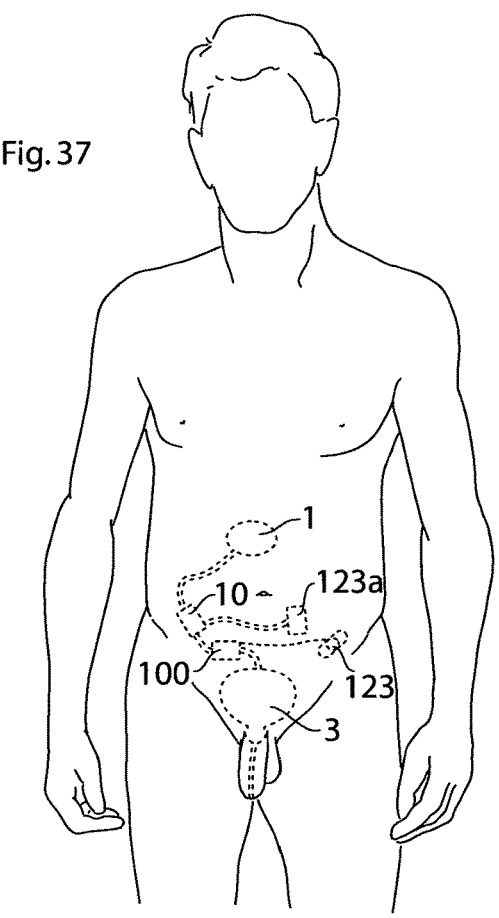
FIG. 37 is general view of an implanted drainage apparatus with a filter in a patient.

As described above the implanted drainage device can be powered by an internal power supply. The same power supply or another power supply can be used to provide energy the filter and or cleaning device 10 as described herein. In FIG. 37 a general view similar to the view in FIG. 32 is shown where the filter and the cleaning device 10 is connected to a power supply. The apparatus in FIG. 37 comprises a first end of the drainage apparatus located in a treatment area 1. The apparatus further comprises a pump 100 adapted to move fluid from the treatment area 1 to a delivery area 3. The treatment area can be any area from which fluid is to be move including but not limited to the abdomen, the lungs and the brain. Similarly the delivery area can be any suitable delivery area within the body, including but not limited to the Urine bladder and the stomach. The apparatus can as stated above further comprise a filter and or a cleaning device 10. The filter and or cleaning device 10 can be powered by an energy source 123a as described above. The energy source can be the same as the energy source 123 powering a pump, but can also be another energy source. The energy source 123a can be energized from outside the patient using a wireless energy transfer device. The energy transfer device can transfer energy in a way suitable such as by inductive energy using coils or ultra sonic energy transfer or by transmitting light through the skin of the patient. Also the fluid passageway from the treatment area to the delivery area can comprise a cleaning device 10 as described above. The cleaning device can in one embodiment be powered by a motor and the motor can then be supplied with energy from the energy source 123a.

Figure 38:
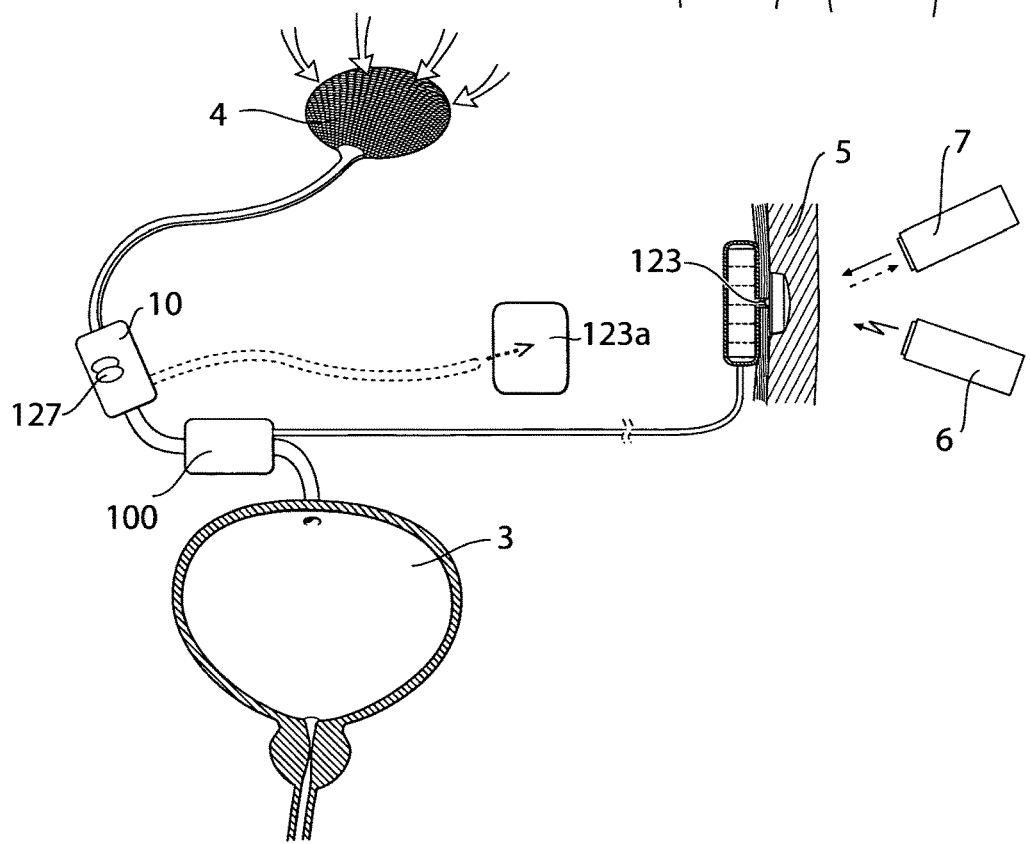
FIG. 38 is a detailed view of a powered filter.

In FIG. 38 the power supply to a filter and a cleaning device 10 is shown in more detail. The view in FIG. 38 corresponds to the view in FIG. 37. However instead of showing the treatment area 1, FIG. 38 shows and end member 4 of the tube located in the treatment area. As is shown in FIG. 38 the energy source 123 and 123a can be energized from outside the skin 5 of a patient by an external energy source 6. The energy source can also receive and transmit information to and from an external signaling device 7. The cleaning device can also be connected to changeable filter cassettes 127. In accordance with one embodiment a dirty filter of a cassette 127 is adapted to be replaced by a new filter of the cassette. The filter can also comprise a net structure.

Figure 39A:
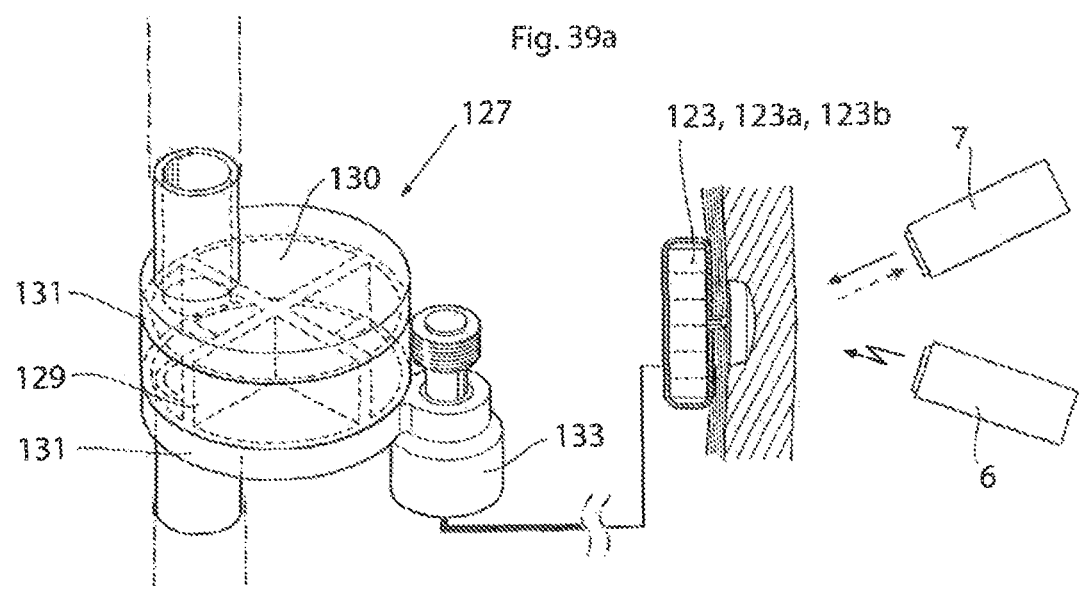
FIGS. 39a and 39b are views of a filter cassette.

In FIG. 39a a cassette 127 for holding filters is shown. The cassette 27 comprises a revolving cylinder 129 having segments 130 each holding a filter. The cylinder 129 is tightly sealed between two supports 131 holding the cylinder 129 in place and providing a tight sealing. The fluid passage way of an implantable drainage apparatus passes through the cassette 127. The cassette is driven by a motor 133 causing the cylinder 129 to revolve at suitable times. The motor is powered by a power supply 123b. The power supply can be a power supply like the power supplies 123 or 123a. In accordance with one embodiment the power supplies 123, 123a and 123b is the one and same power supply. As with the power supplies 123 and 123a, the power supply 123b can receive wireless energy in a suitable form, including but not limited to inductive energy ultrasonic energy, light energy or any other form of wireless energy set out above. The energy is supplied by an external wireless energy transmitter 6 adapted to transmit energy through the skin 5 of a patient having the cassette 127 implanted. The power supply 132b can also comprise a control unit as described above for controlling the revolving cassette 127. The control unit can provide feedback to the outside and receive input data from an external transceiver 7 in a manner similar to the control unit used in conjunction with control of the pump.

Figure 39B:
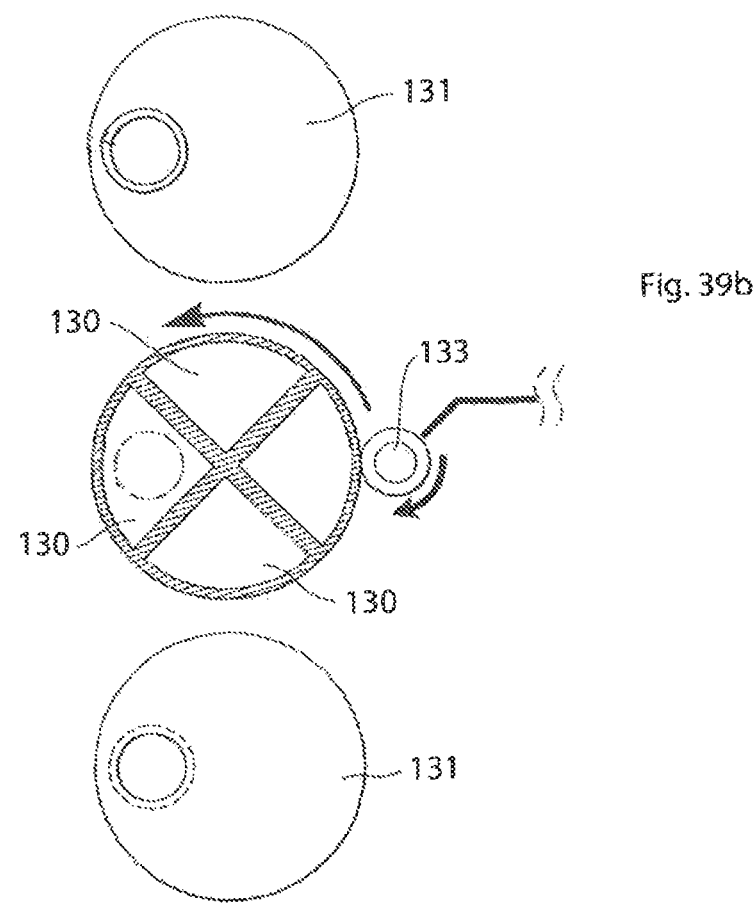

In FIG. 39b the cassette 127 is shown from the side with the supports 131 and the revolving cylinder spaced apart is a disassembled view.

Figure 40A:
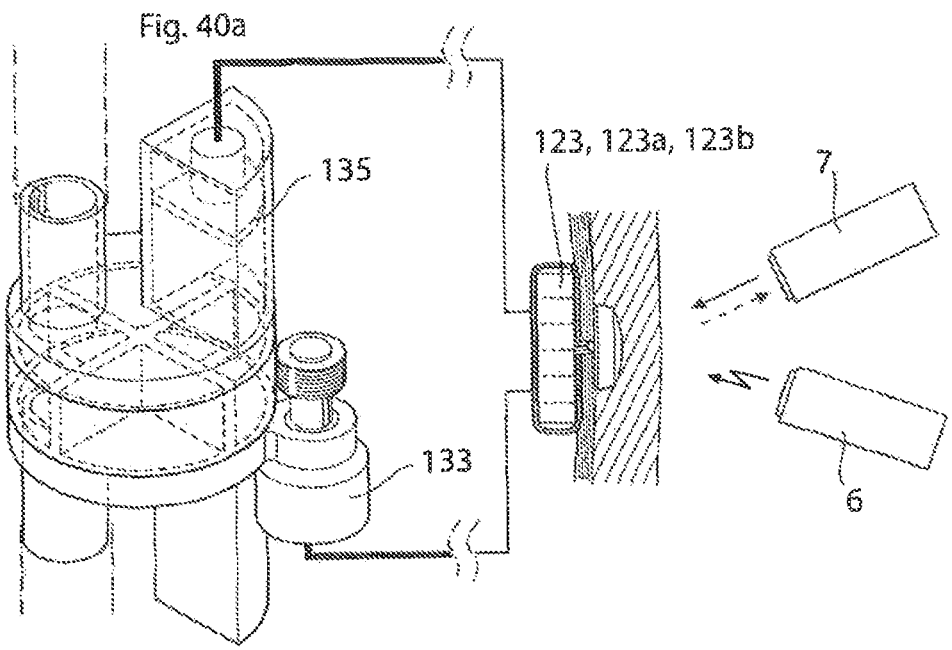
FIGS. 40a and 40b are views of a filter cassette.

In FIG. 40a an alternative embodiment of the cassette 127 is shown. The view in FIG. 39a is similar to the view in FIG. 39a. In the embodiment in FIG. 40a a magazine 135 having a number of cylinders 129 stored therein is provided. Hereby a cylinder 129 can by replaced by shifting the cylinders in the magazine 135. In one embodiment the cylinders are shifted by pressurized air.

Figure 40B:
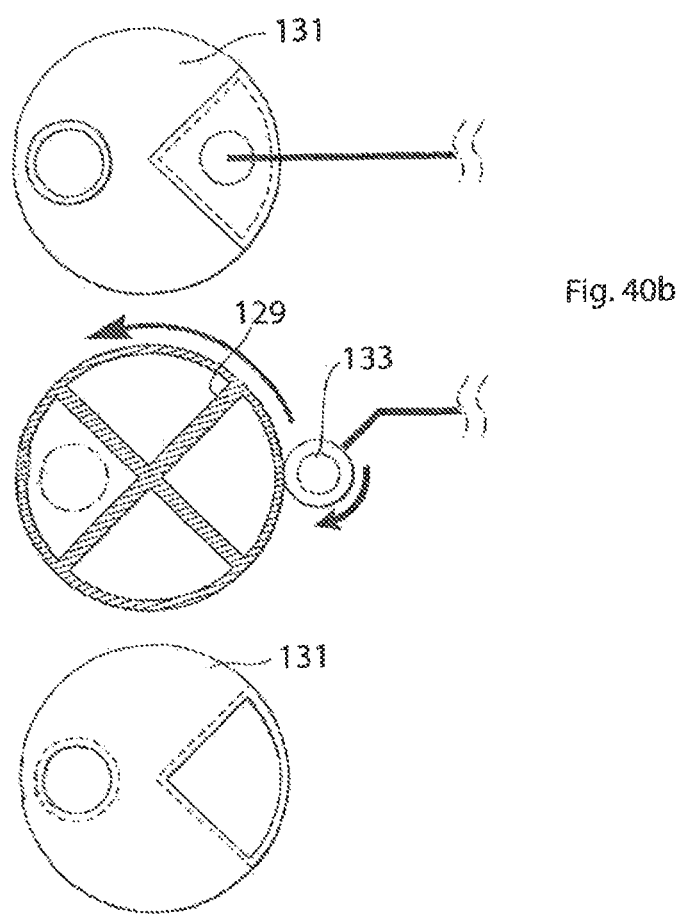

In FIG. 40b the cassette 127 is shown from the side with the supports 131 and the revolving cylinder spaced apart is a disassembled view.

Figure 41:
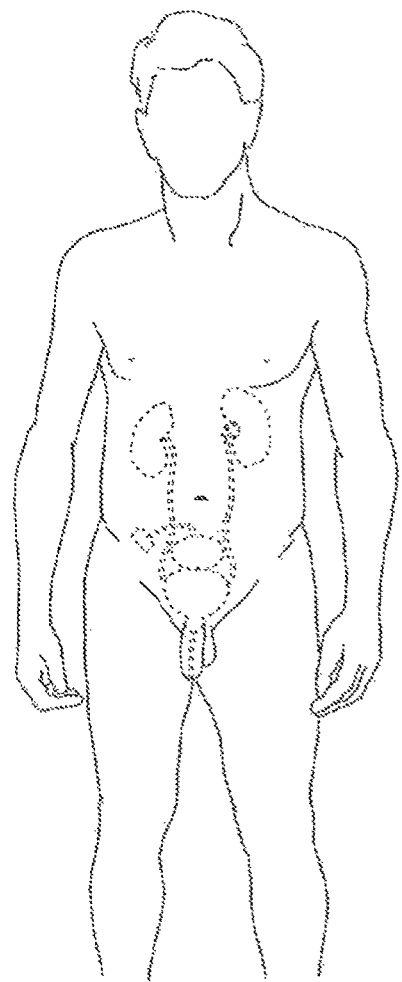
FIG. 41 shows the placement in the body of a hydraulic treatment embodiment.
Figure 42:
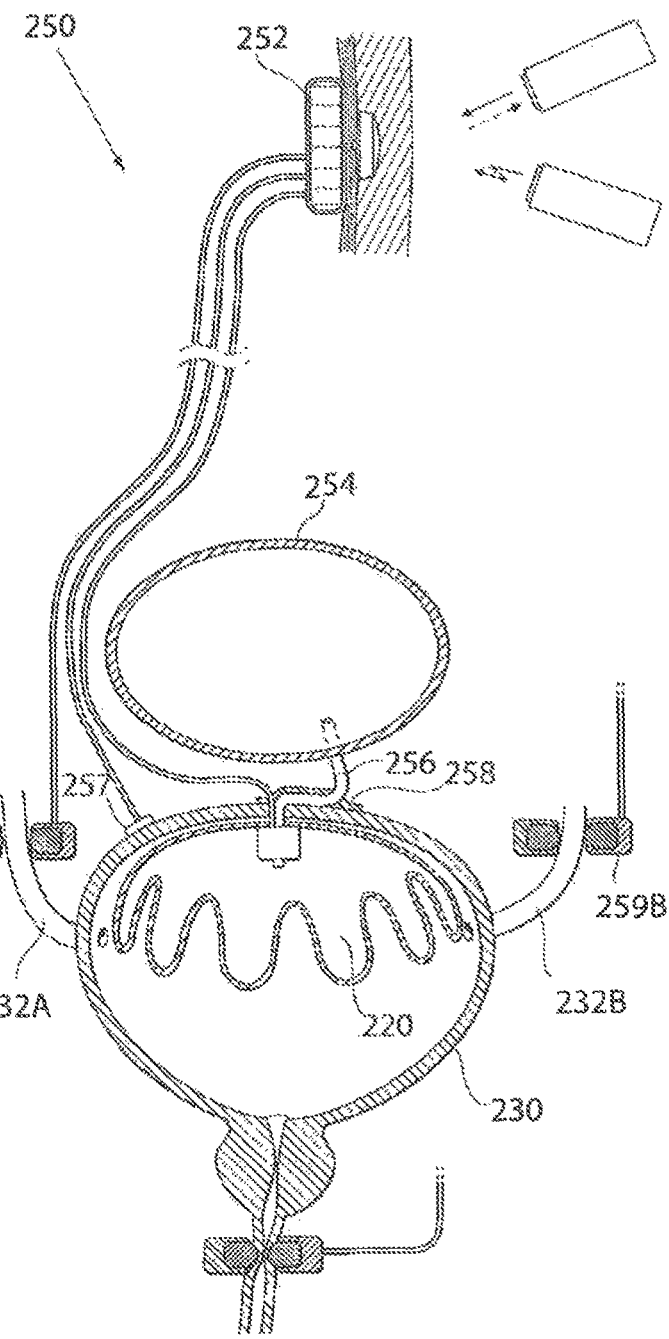

FIGS. 41-43 illustrate an embodiment using hydraulic treatment fluid according to the invention.

By reference to FIG. 41 and FIG. 42, the apparatus has an expandable member 220 with a cavity for accommodating hydraulic fluid that is placed inside the urinary bladder 230 which contains urine arrived from the ureters 232A, 232B. A control device 250 operates the expansion and thereby the volume of the expandable member. The control device 250 has a control assembly 252 connected to a reservoir 254 for hydraulic fluid which is connected to the expandable member with an interconnecting device 256 for transporting hydraulic fluid between the reservoir 254 and the expandable member 220. The interconnecting device 256 is a tube-shaped device surgically incised through the wall of the urinary bladder and attached thereto with tunneling technique whereby the bladder wall is sutured to itself The interconnecting device is supported by the net 258 which seals fixates by admitting tissue in-growth. The control assembly 254 is located in the patient and includes a number functional elements necessary for operating the apparatus, such as an operating pump 259 for the hydraulic fluid, a source of energy for driving the operating pump and other energy consuming parts of the apparatus, and control functions including wireless communication with an external control unit. A suitable control assembly is described in more detail in the parallel patent application no. One or more parts of the control device may be implanted subcutaneously or in the abdominal cavity or the pelvic region or any other suitable place inside the body. The embodiment depicted in FIG. 42 is adapted for a patient suffering from a complication where the urinary sphincter is permanently closed. For this reason, the expandable member 220 of the apparatus needs to exert a considerable pressure (about 60-80 cm water pressure) to force urine out from the bladder and urine may thereby backflow through ureters 232A, 232B with potential risks for damaging the kidneys. To prevent from any such complications, the control device is provided with restriction devices 259A, 259B arranged to temporarily contract the ureters and close them during the operation of discharging urine with the expandable member. The restriction devices are operated from the control assembly in manner to perform their temporary contraction during the discharge performance. Suitable mechanical or hydraulically operated restriction devices and their control are described in more detail in European Patents Nos. EP 1253880; EP 1284691; and EP 1263355. The urine pressure in the ureter is normally around 50 cm water, however short term pressure increase is most likely not damaging the kidneys and therefore the restriction devices 259A and 259B may be omitted.

When the pump is not pumping to fill the expandable member and if the passage-way between the reservoir and the expandable member is free, then the expandable member may be emptied by urine filling the bladder. Another alternative is that the pump starts in steps to empty the expandable member for example pressure controlled or controlled by any other input sensor as mentioned elsewhere. In another embodiment a second connection may be established between the expandable member and the reservoir). If the pumping volume capacity is clearly much larger than the emptying capacity of the second connection this connection may always stand open.

By reference to FIG. 42 and FIG. 43, the apparatus in operated by activating the operating pump of the control assembly 254 which is operable in response from a signal from a remote control 253 The control assembly can also be connected to a pressure sensor 257 for monitoring the urinary pressure of the bladder. Several different type of input sensors may be used determining for example stretching or bending or pressure in the urine bladder wall or for example sensing volume or pressure inside the urine bladder. Most likely these sensors is only indirect causing the bladder to be emptied by presenting an alarm for the patient informing that it is time to empty the bladder. Such an alarm is generated audible or visually. The remote control may include a subcutaneous switch for controlling the emptying of the bladder or communicating via the body used as a wire or with wireless communication. The operating pump now transports hydraulic fluid from the reservoir 254, through the interconnection device 256 to the cavity of the expandable member 220, which thereby increases in volume in the urinary bladder and discharges urine through the urethra at a pressure that overcomes the closing force of the urethral sphincter, so voiding of the urinary bladder is accomplished. During this operation the control assembly operates to close restriction device 259A, 259B to prevent any urinary backflow in the ureters. When the discharging performance is finished and the operating pump is inactive, the restriction devices 259A, 259B are released so urine can refill the urinary bladder. By the pressure of the refilled urine, the expandable member 220 subsequently collapses to retain a shape as shown in FIG. 42 when ready for a new performance as monitored by the pressure sensor.

Some patients having urinary retention also have urinary incontinence. In such a case a separate urinary sphincter is included in the system, a restriction device closing the urethra until the patient wants to urinate. In such a case lower pressure is needed to empty the bladder because the no force would be needed to open the sphincter by intra bladder pressure. In this case the restriction devices 259A and 259B may be omitted.

The reservoir 254 may be placed anywhere inside the body, however preferable in the abdominal cavity, maybe placed onto the urine bladder or in the pelvic region. The amount of liquid in the reservoir may be calibrated with fluid by using a injection port placed inside the body within reach from a special injection port needle. The reservoir may also be omitted and only the injection port may be used to fill and empty the expandable member. With the described embodiment it is also conceivable to control the duration/force of the urine discharge process, e.g. that data from the pressure sensor measuring the urinary pressure or easier the pressure inside the expandable member in the bladder controls the operation pump by logic in the control assembly. It should be noted that the expandable member may be elastic or only flexible, within the used pressure inside the same.

It should be noted that any embodiment or part of embodiment or feature or method or associated system or part of system described herein may be combined in any combination.

The invention claimed is:

1. An apparatus for moving a fluid to or from a cavity in a body of a human or mammal patient, comprising:
    a fluid movement device;
    an energy source adapted to supply energy to said fluid movement device;
    at least one connecting tube having a tube end, the at least one connecting tube being connected to the fluid movement device; and
    a flexible patch;
wherein:
    the fluid movement device and the at least one connecting tube form a fluid moving arrangement adapted to be implanted inside the body of the human or mammal patient;
    the tube end is adapted to be inserted into an organ of the patient;
    at least a portion of the apt least one connecting tube is adapted to be invaginated in a wall of the organ so as to interconnect a treatment area of the body with a delivery area;
    the fluid movement device is adapted to move fluid from the treatment area via the at least one connecting tube to the delivery area;
    the flexible patch comprises a net structure adapted to be overgrown by human fibrotic tissue when implanted in the human or mammal patient; and
    the flexible patch is arranged at a distance from the tube end to allow the flexible patch to be attached to an outer surface of the organ when the at least one connecting tube is invaginated in the wall of the organ, wherein the flexible patch is further adapted to be arranged with a lateral extension along the outer surface of the organ so as to fixate and seal the at least one connecting tube to the organ by means of overgrowth of human fibrotic tissue.

2. The apparatus for moving a fluid to or from a cavity in a human or mammal patient according to claim 1, wherein the net structure is sealed around the at least one connecting tube.

3. The apparatus for moving a fluid to or from a cavity in a human or mammal patient according to claim 1, wherein the net structure is provided with holes having a diameter suitable for overgrowth by tissue.

4. The apparatus for moving a fluid to or from a cavity in a human or mammal patient according to claim 3, wherein the diameter of the holes is smaller than 2.5 mm.

5. The apparatus for moving a fluid to or from a cavity in a human or mammal patient according to claim 3, wherein the diameter of the holes is smaller than 1.5 mm.

6. The apparatus for moving a fluid to or from a cavity in a human or mammal patient according to claim 3, wherein the diameter of the holes is smaller than 0.5 mm.

7. The apparatus for moving a fluid to or from a cavity in a human or mammal patient according to claim 1, wherein the at least one connecting tube comprises:
    at least one first connecting tube connected to said fluid movement device adapted to drain urine from a renal part of a kidney accumulating urine, and
    at least one second connecting tube adapted to be connected to an urine bladder and passing through a wall of said urine bladder, farther adapted to be invaginated in the wall of the urine bladder thereby creating a tunnel around the second connecting tube, the at least one first connecting tube, the at least one second connecting tube and the fluid movement device being implantable in the body and adapted to move urine from the renal part of the kidney to the urine bladder, using power from said energy source, wherein said at least one second connecting tube includes said net structure adapted to seal a tube passageway out from the urine bladder, when invaginated by the wall of the urine bladder, by overgrowth of human tissue in an outer opening of the tunnel.

8. The apparatus for moving a fluid to or from a cavity in a human or mammal patient according to claim 1, wherein the at least one connecting tube comprises:
    least one first connecting tube connected to said fluid movement device adapted to drain liquid from a hydrocephalus in a brain area, and
    at least one second connecting tube adapted to be connected to an abdomen, the at least one first connecting tube, the at least one second connecting tubes, and the fluid movement device, being adapted to be implanted inside the body, the fluid movement device further being adapted to move liquid from the hydrocephalus to the abdomen, using power from said energy source.

9. The apparatus for moving a fluid to or from a cavity in a human or mammal patient according to claim 1, wherein the at least one connecting tube comprises:
    at least one first connecting tube connected to said fluid movement device adapted to drain liquid from an ascites in an abdomen, and
    at least one second connecting tube adapted to be connected to a lymphatic system of the body, the at least one first connecting tube, the at least one second connecting tube, and the fluid movement device being adapted to be implanted inside the body, the fluid movement device further being adapted to move liquid from the ascites in the abdomen into the lymphatic system, using power from said energy source.

10. The apparatus for moving a fluid to or from a cavity in a human or mammal patient according to claim 1, wherein the at least one connecting tube comprises:
    at least one first connecting tube connected to said fluid movement device adapted to drain liquid from ascites in an abdomen, and
    at least one second connecting tube adapted to be connected to an urine bladder of the body and passing through a wall of said urine bladder, further adapted to be invaginated in the wall of the urine bladder thereby creating a tunnel around the tube, the at least one first and second connecting tubes and the fluid movement device being adapted to be implanted inside the body, the fluid movement device further being adapted to move liquid from the ascites in the abdomen into the urine bladder, using power from said energy source, wherein said second connecting tube includes said net structure adapted to seal the tube passageway out from the urine bladder, when invaginated by the same, by overgrowth of human tissue in an outer opening of the tunnel.

11. The apparatus for moving a fluid to or from a cavity in a human or mammal patient according to claim 1, wherein the at least one connecting tube comprises:
    at least one first connecting tube connected to said fluid movement device adapted to drain liquid from a thoraxial cavity, and
    at least one second connecting tube adapted to be connected to an abdomen, the at least one first and second connecting tubes and the fluid movement device being adapted to be implanted inside the body, the fluid movement device further being adapted to move liquid from a thorax to the abdomen, using power from said energy source.

12. The apparatus for moving a fluid to or from a cavity in a human or mammal patient according to claim 11, wherein the net structure is provided with holes having a diameter suitable for overgrowth by tissue.

13. The apparatus for moving a fluid to or from a cavity in a human or mammal patient according to claim 12, wherein the diameter of the holes is smaller than 2.5 mm.

14. The apparatus for moving a fluid to or from a cavity in a human or mammal patient according to claim 12, wherein the diameter of the holes is smaller than 1.5 mm.

15. The apparatus for moving a fluid to or from a cavity in a human or mammal patient according to claim 12, wherein the diameter of the holes is smaller than 0.5 mm.

16. The apparatus for moving a fluid to or from a cavity in a human or mammal patient according to claim 1, comprising:
    a filter for filtering the fluid being moved by the fluid movement device, and
    a cleaning device to clean the filter.

17. The apparatus for moving a fluid to or from a cavity in a human or mammal patient according to claim 1, wherein the cleaning device is adapted to move any cleaned particles outside a flow passageway wherein the fluid is passing.

18. The apparatus for moving a fluid to or from a cavity in a human or mammal patient according to claim 1, wherein a tube area between the net structure and the organ is adapted to be invaginated in the organ wall.

19. The apparatus for moving a fluid to or from a cavity in a human or mammal patient according to claim 1, wherein the net structure is sealed around the tube.

20. The apparatus for moving a fluid to or from a cavity in a human or mammal patient according to claim 1, adapted to receive wireless energy from an energy transmission device for at least one of;
    to recharge the energy source adapted to supply energy to said fluid movement device, and
    to supply energy to the fluid movement device, via an energy transforming device, adapted to transform the wireless energy to a current for supplying energy to said fluid movement device.

21. The apparatus for moving a fluid to or from a cavity in a human or mammal patient according to claim 1, further comprising;
    an internal control unit and
    a sensor,
wherein the apparatus is further adapted to send an information from the sensor to the internal control unit to give feedback related to at least one of a functional parameter of the apparatus and a physical parameter of the patient, the internal control unit adapted to act in response to the information to regulate the fluid movement device of said apparatus for moving a fluid to or from a cavity in a human or mammal patient.

22. A method of securing at least one connecting tube for use in an implantable device for implantation in a human or mammal body, wherein the at least one connecting tube is adapted to move a body fluid or a hydraulic treatment fluid from one part of the human or mammal body, via the at least one connecting tube to another part of the human or mammal body, the at least one connecting tube having a distal end adapted to be located in an organ of the human or mammal body for drainage of the body fluid or in a reservoir for movement of the hydraulic treatment fluid, from a treatment area of the human or mammal body into the organ, the method comprising the steps of:
    cutting the skin,
    dissecting the treatment area,
    opening a hole in the organ,
    placing an end of the at least one connecting tube in the organ,
    securing the at least one connecting tube on an outside of the organ by invaginating the at least one connecting tube using sutures or staples, thus creating an invaginated tunnel around the at least one connecting tube, wherein said at least one connecting tube comprises a flexible patch comprising a net material secured to said at least one connecting tube, the method further comprising,
    placing the net material in connection to an opening of the invaginated tunnel such that the patch has a lateral extension along an outer surface of the organ, and
    securing the net material to the outer surface of the organ.

* * * * *